United States Patent [19]

Schmitt-Willich et al.

[11] Patent Number: 5,681,543
[45] Date of Patent: Oct. 28, 1997

[54] POLYMER-BONDED COMPLEXING AGENTS AND PHARMACEUTICAL AGENTS CONTAINING THEM FOR MRI

[75] Inventors: Heribert Schmitt-Willich; Julius Deutsch; Heinz Gries; Jürgen Conrad; Reinhard Neumeier, all of Berlin, Germany

[73] Assignee: Shering Aktiengesellschaft, Berlin, Germany

[21] Appl. No.: 289,341

[22] Filed: Aug. 10, 1994

Related U.S. Application Data

[63] Continuation of Ser. No. 779,732, Oct. 23, 1991, abandoned, which is a continuation-in-part of Ser. No. 317,218, Feb. 28, 1989, abandoned.

[30] Foreign Application Priority Data

Feb. 29, 1988 [DE] Germany ............... 38 06 795.1

[51] Int. Cl.⁶ ............................................. A61B 5/055
[52] U.S. Cl. ................... 424/934; 424/935; 424/936; 556/50; 556/63; 556/107; 556/117; 556/134; 556/148; 436/173; 436/806; 514/6; 514/184; 514/836; 128/653.4; 534/15; 534/16
[58] Field of Search .......................... 424/9, 9.34, 9.35, 424/9.36; 436/173, 806; 128/653.4, 654; 514/184, 836, 6; 534/15, 16; 556/50, 63, 107, 117, 134, 148

[56] References Cited

U.S. PATENT DOCUMENTS

| | | | |
|---|---|---|---|
| 4,647,447 | 3/1987 | Gries et al. | 424/9 |
| 4,675,381 | 6/1987 | Bichon | 530/345 |
| 4,728,575 | 3/1988 | Gamble et al. | |
| 4,957,939 | 9/1990 | Gries et al. | 514/492 |
| 4,963,344 | 10/1990 | Gries et al. | 424/9 |
| 4,986,980 | 1/1991 | Jacobsen . | |
| 4,999,445 | 3/1991 | White et al. | 556/138 |
| 5,021,236 | 6/1991 | Gries et al. | 424/9 |
| 5,155,215 | 10/1992 | Ranney | 534/16 |
| 5,213,788 | 5/1993 | Ranney | 424/9 |
| B1 4,963,344 | 8/1992 | Gries et al. | 424/9 |

FOREIGN PATENT DOCUMENTS

| | | |
|---|---|---|
| 0243929 | 4/1987 | European Pat. Off. . |
| 0 268 707 | 6/1988 | European Pat. Off. . |
| 0 277 088 | 8/1988 | European Pat. Off. . |
| 164458 | 7/1990 | Norway . |
| 169103 | 2/1992 | Norway . |

OTHER PUBLICATIONS

Schmiedl, U et al. AJR 147:1263–1270 (1986).
Gibby, Wa et al. Invest. Radiol. 24:302–309 (1989).
Hallaway, PE Proc. Nat. Acad. Sci. 86:10108–10112 (1989).
Abstract of AU-A-10649/88 (in the English language).
Manabe et al., "High-level conjugation of chelating agents onto immunoglobulins: use of an intermediary poly(L-lysine)-diethylenetriaminepenta-acetic acid carrier," Biochimica et Biophysica Acta 883 (1986) 460–467.
Schmiedl et al, "Albumin Labeled with Gd-DTPA . . . Imaging Studies" Radiology, vol. 162, No. 1, pp. 205–210 (1987).
Torchilin et al, "Monoclonal Antibody Modification . . . Antigen Binding" Hybridoma, vol. 6, No. 3, pp. 229–240 (1987).
Alfidi et al, "Preliminary Experimental Results . . . Resonance Scanner", Radiology, vol. 143, No. 1, pp. 175–181 (Apr. 1982).

*Primary Examiner*—Gary E. Holliden
*Attorney, Agent, or Firm*—Millen, White, Zelano & Branigan, P.C.

[57] ABSTRACT

Polymers comprising a ligand containing a carboxylic acid group, optionally at least one ion of an element of the atomic numbers 21–29, 42, 44 or 57–83 as well as optionally cations of inorganic and/or organic bases, amino acids or amino acid amides are valuable complexing agents and complexes for diagnosis.

18 Claims, No Drawings

POLYMER-BONDED COMPLEXING AGENTS AND PHARMACEUTICAL AGENTS CONTAINING THEM FOR MRI

RELATED COPENDING APPLICATIONS

This application is a continuation of application Ser. No. 07/779,732, filed Oct. 23, 1991, abandoned which is a continuation-in-part of application Ser. No. 07/317,218, filed Feb. 28, 1989 (now abandoned).

BACKGROUND OF THE INVENTION

This invention relates to new polymer complexes, agents containing these compounds, their use in diagnosis as well as processes for the production of these compounds and agents.

The use of complexing agents or complexes or their salts in medicine has been known for a long time. There can be mentioned as examples the following:

Complexing agents as stabilizers of pharmaceutical preparations, complexes and their salts as auxiliary agents for administration of poorly soluble ions (e.g., iron), complexing agents and complexes (preferably calcium or zinc), optionally as salts with inorganic and/or organic bases, as antidotes for poisoning in case of inadvertent incorporation of heavy metals or their radioactive isotopes and complexing agents as auxiliary agents in nuclear medicine by use of radioactive isotopes such as $^{99m}Tc$ for scintigraphy are known.

Paramagnetic complex salts as diagnostic agents, mainly as NMR diagnostic agents, were recently proposed in DE-OS 3401052.

These complexes or complex salts are quite easily compatible and ensure to the greatest possible extent complete excretion of the paramagnetic ions. However, the drawback is that they are distributed only unspecifically in the extracellular space and therefore are suitable only in exceptional cases for recognition of pathologically changed tissues.

The attempt to solve at least one part of this problem by use of complexing agents, which, on the one hand, are bonded by ionic bonding on the respective suitable metal (see below) as well as, on the other hand, by bonding on a functional group or a nontoxic molecule that is as organ-specific as possible acting as a carrier molecule, so far has been successful only in a very limited way.

Thus, for example, the number of paramagnetic centers in the complexes, which are described in European patent applications No. 88 695 and No. 150 884, are not sufficient for an organ-specific imaging.

If the number of necessary metal ions is increased by repeated introduction of complexing units into a macromolecule, this technique is always linked with an intolerable impairment of the affinity and/or specificity of this macromolecule [(J. Nucl. Med. 24, 1158 (1983)].

SUMMARY OF THE INVENTION

Therefore for various purposes there is a need for stable, easily soluble but also better compatible, easily accessible complex compounds, which contain as great a number as possible of the necessary metal ions in the complex, without their affinity and/or specificity being lost. This invention makes available such compounds and agents, and provides a process as simple as possible for their production.

It has been found that polymer complexes, which comprise recurring units comprising a ligand containing carboxylic acid groups and optionally provided with amide, hydrazide and/or alkylated or acylated imino subunits, and optionally at least one ion of an element of atomic numbers 21–29, 42, 44 or 57–83 as well as optionally cations of inorganic and/or organic bases, amino acids or amino acid amides, in a surprising way are exceptionally suitable for the production of NMR, X-ray and ultrasonic diagnostic media, since above all they can contain the number of metal ions stably bonded in the complex that are necessary for this use.

The polymers according to the invention exhibit as polymer units complexing structures of general formula I $$-(S_1AS_2)_s-(S_3A'S_4)_t-, \qquad (I)$$
$$\begin{array}{cc} | & | \\ U & W \\ | \\ V \\ | \\ K \end{array}$$

in which

A and A' each mean

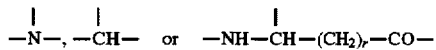

with r meaning the numbers 0 or 1,
s means whole numbers from 7 to 20,000,
t means whole numbers from 0 to 20,000,
U means a direct bond, the group

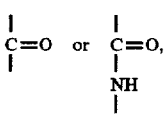

V, $S_1$, $S_2$, $S_3$ and $S_4$ each mean a straight-chain, branched, saturated or unsaturated $C_0$–$C_{20}$ hydrocarbyl group optionally containing imino, phenylene, phenyleneoxy, phenyleneimino, amide, hydrazide, ester group(s), oxygen, sulfur and/or nitrogen atom(s) optionally substituted by hydroxy, mercapto, imino, epoxy, oxo, thioxo and/or amino group(s), K means a complexing agent of general formula IA, IB, IC or ID

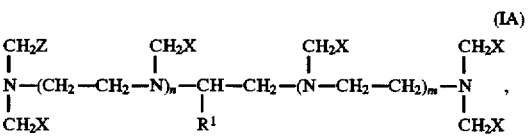

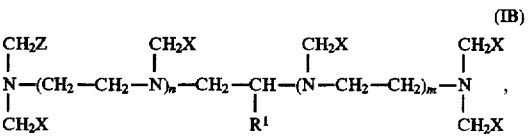

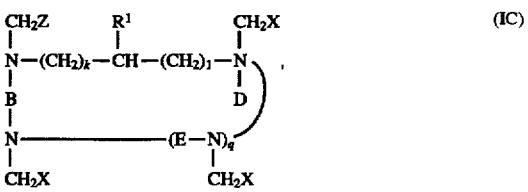

-continued $$\begin{array}{ccc} CH_2X & CH_2X \\ | & | \\ N-CHR^3-CHR^4-N & , \\ | & | \\ CH_2X & CH_2X \end{array} \quad (II)$$

in which n and m each stand for the numbers 0, 1, 2, 3 or 4, and n and m together amount to no more than 4, k stands for the numbers 1, 2, 3, 4 or 5, l stands for the numbers 0, 1, 2, 3, 4 or 5, q stands for the numbers 0, 1 or 2, X independently of one another each stand for the radical —COOH or V', in which V' means the radical V exhibiting on the end a functional group or a biomolecule or macromolecule bonded by this functional group, in which, if the molecule contains V', at least 0.1% of the substituents X stand for V' and, typically at most about 10%, B, D and E, which are the same or different, each stand for the group $$-(CH_2)_u-(CH)_v-(CH_2)_l$$
$$\qquad\quad | \\ \qquad\quad R^2$$

with $R^2$ meaning hydrogen or a straight-chain, branched, saturated or unsaturated $C_1$–$C_{20}$ hydrocarbyl group optionally containing oxygen and/or nitrogen atom(s) optionally substituted by hydroxy and/or amino group(s), u means the numbers 0, 1, 2, 3, 4 or 5, v means the numbers 0 or 1, and B, D and E each contain at least 2 and at most 5 carbon atoms in their chain, Z stands for the group $$\begin{array}{c} O \\ \| \\ -C- \end{array}$$

or the radical X, $R^1$ stands for a direct bond or a hydrogen atom, $R^3$ and $R^4$ together stand for a dimethylenemethine or trimethylenemethine (CH—$CH_2$—$CH_2$—$CH_2$—) group optionally substituted by 1–2 hydroxy or 1–3 $C_1$–$C_4$ alkyl groups, provided that Z then stands only for the group $$\begin{array}{c} O \\ \| \\ -C-, \end{array}$$

if $R^1$ at the same time means a hydrogen atom, and that Z then stands only for the radical X, if $R^1$ at the same time means a direct bond, W means a hydrogen atom, biotin, avidin, avidin-biotin antibodies, avidin-biotin antibody fragments, the group $U_w$—$V_w$—$K_w$, and $U_w$, $V_w$ and $K_w$ each have one of the meanings named for U, V and K, V' or the group $$\begin{array}{c} -C-V' \\ \| \\ O \end{array}$$

provided that optionally a part of the COOH groups is present as ester and/or amide.

With respect to Group W, when this group contains a biomolecule or macromolecule structure, it is preferred that such structure not be a monoconal antibody linked via succinic acid groups. See Torchilin et al., Hybridoma, Volume 6, No. 3, pages 229–240 (1987).

By a $C_o$ alkylene chain is to be understood a direct bond.

In the polymer backbone, at most, two, preferably no consecutive N atoms are bonded together, e.g., via a hydrazide bond.

Typically each recurring unit of the polymer will contain at least 2 COOH groups as X's.

s can be 7 to 20,000, e.g., at least 8, 9, 10, 50, 100, 500, 1,000, 5,000, 10,000, etc.

t can be 0–20,000, e.g., at least 1, 2, 5, 8, 9, 10, 50, 100, 500, 1,000, 5,000, 10,000, etc.

As preferred polymer units there can be mentioned the complexing structures of general formula I:

$$\begin{array}{c} -(NH-CH-CO)_s-(NH-CH-CO)_t- \\ \qquad\quad | \qquad\qquad\qquad\qquad | \\ \qquad\quad (CH_2)_4 \qquad\qquad\qquad W \\ \qquad\quad | \\ \qquad\quad NH \\ \qquad\quad | \\ \qquad\quad K \end{array} \quad (Ia)$$

If the medium according to the invention is intended for use in NMR diagnosis, the central ion of the complex salt is paramagnetic. This is especially the two valent and three valent ions of the elements of atomic numbers 21–29, 42, 44 and 57–70. Suitable ions are, for example, chromium(III), manganese(II), iron(II), cobalt(II), nickel(II), copper(II), praseodymium(III), neodymium(III), samarium(III) and ytterbium(III) ions. Because of their very strong magnetic moment, the gadolinium(III), terbium(III), dysprosium(III), holmium(III), erbium(III) and iron(III) ions are especially preferred.

If the medium according to the invention is intended for use in X-ray diagnosis, the central ion is derived from an element of higher atomic number to achieve a sufficient absorption of the X rays. It has been found that for this purpose diagnostic media, which contain a physiologically compatible complex salt with central ions of elements of atomic numbers 21–29, 42, 57–83, are suitable; this is, for example, the lanthanum(III) ion and the above-named ions of the lanthanide series.

The polymer complexes according to the invention contain at least one ion of an element of the above-named atomic number.

Different ions can be present in one complex.

The hydrocarbylene, e.g., alkylene, groups standing for V and $S_1$–$S_4$, as well as the alkyl groups standing for $R^2$, R and $R^1$, can be straight-chain, branched, cyclic, aliphatic, aromatic or arylaliphatic and exhibit up to 20 carbon atoms. Straight-chain mono- to deca-methylene groups as well as $C_1$–$C_4$ alkylenephenyl(ene) groups are preferred. For illustration the following "alkylene" groups can be mentioned:
—$CH_2$—O—$C_6H_4$—$CH_2$—; —$CH_2$—CH(OH)—$CH_2$—O—$C_6H_4$—$CH_2$—; —C(=NH)—O—$C_6H_4$—$CH_2$—; —($CH_2$)$_4$—NH—CO—$CH_2$—O—$C_6H_4$—$CH_2$—; —($CH_2$)$_4$—NH—$CH_2$—CH(OH)—$CH_2$—O—$C_6H_4$—$CH_2$—; —($CH_2$)$_3$—O—$C_6H_4$—$CH_2$—; —$CH_2$—CO—

NH—(CH$_2$)$_3$—O—CH$_2$—; —CH$_2$—CO—NH—NH—;
—CH$_2$—CONH—(CH$_2$)$_2$—; —CH$_2$—CO—NH(CH$_2$)$_{10}$—; —CH$_2$—CONH—(CH$_2$)$_2$—S—; —(CH$_2$)$_4$—NH—CO—(CH$_2$)$_8$—; —CH$_2$—CO—NH—(CH$_2$)$_3$—NH—; —(CH$_2$)$_3$—NH;

The alkyl portions of the former groups can be saturated or unsaturated (double or triple bonds).

Preferred functional groups, which are on the end of the V″ or V′ hydrocarbylene group, are for example the maleimidobenzoyl, 3-sulfomaleimidobenzoyl, 4-(maleimidomethyl)-cyclohexylcarbonyl, 4-[3-sulfo-(maleimidomethyl)-cyclohexylcarbonyl], 4-(p-maleimidophenyl)-butyryl, 3-(2-pyridildithio)-propionyl, methacryloyl-(pentamethylene)amido, bromoacetyl, iodoacetyl, 3-iodopropyl, 2-bromoethyl, 3-mercaptopropyl, 2-mercaptoethyl, phenyleneisothiocyanate, 3-aminopropyl, benzyl ester, ethyl ester, t-butyl ester, amino, C$_1$–C$_6$ alkylamino, aminocarbonyl, hydrazino, hydrazinocarbonyl, maleimido, methacrylamido, methacryloylhydrazinocarbonyl, maleimidamidocarbonyl, halo, mercapto, hydrazinotrimethylene-hydrazinocarbonyl, aminodimethyleneamidocarbonyl, bromocarbonyl, phenylenediazonium, isothiocyanate, semicarbazide, thiosemicarbazide groups.

For illustration some selected groups are listed:

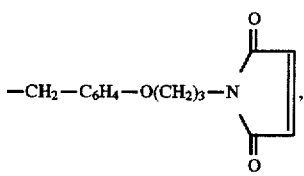

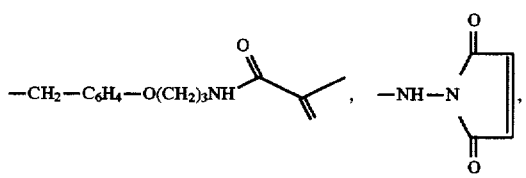

—CH$_2$—C$_6$H$_4$—O(CH$_2$)$_5$CO$_2$CH$_2$C$_6$H$_5$,

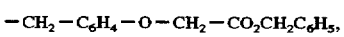
—CH$_2$—C$_6$H$_4$—O—CH$_2$—CO$_2$CH$_2$C$_6$H$_5$,

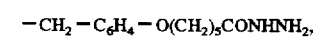
—CH$_2$—C$_6$H$_4$—O(CH$_2$)$_5$CONHNH$_2$,

—CH$_2$—C$_6$H$_4$—O(CH$_2$)$_4$—SH, —CH$_2$—C$_6$H$_4$—O(CH$_2$)$_3$NHNH$_2$,

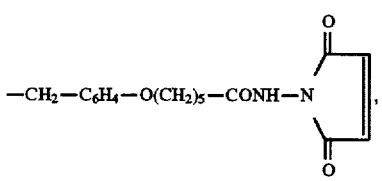
—CH$_2$—C$_6$H$_4$—O(CH$_2$)$_3$Br,

—CH$_2$—C$_6$H$_4$—O(CH$_2$)$_5$CONHNH—(CH$_2$)$_3$—NHNH$_2$,

—CH$_2$—NHNH$_2$, —CH$_2$—SH, —CH$_2$CONHNH$_2$,

—(CH$_2$)$_3$SH, —CH$_2$—C$_6$H$_4$—O—CH$_2$COBr, —C$_6$H$_4$NHCOCH$_2$Br,

-continued

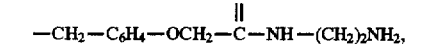

—CH$_2$—C$_6$H$_4$—NH$_2$, —C$_6$H$_4$—N$_2$, —C$_6$H$_4$NHCS,

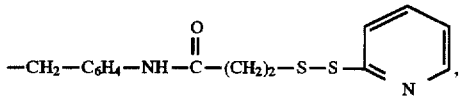

—NHCO—NH—NH$_2$, —NHCS—NH—NH$_2$,

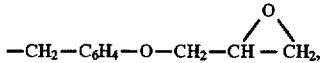

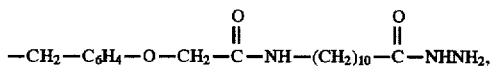

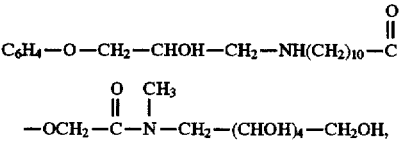

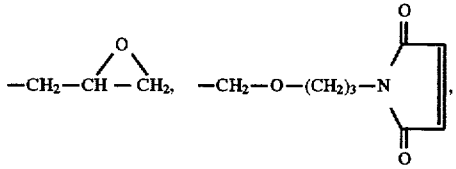

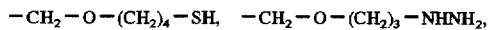

—CH$_2$—O—(CH$_2$)$_4$—SH, —CH$_2$—O—(CH$_2$)$_3$—NHNH$_2$,

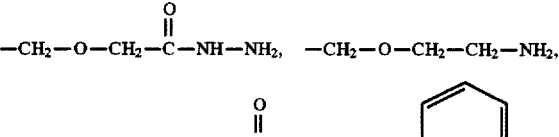

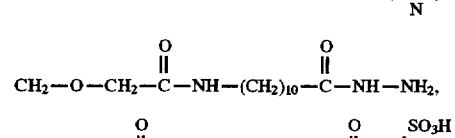

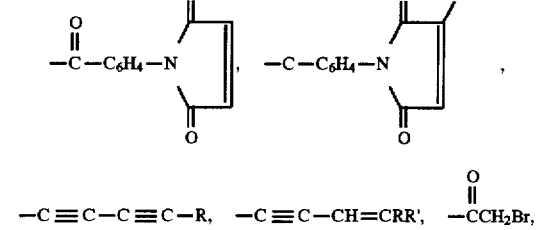

—C≡C—C≡C—R, —C≡C—CH=CRR′, —CCH$_2$Br,

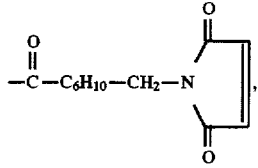

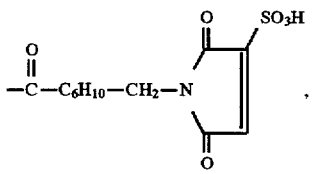

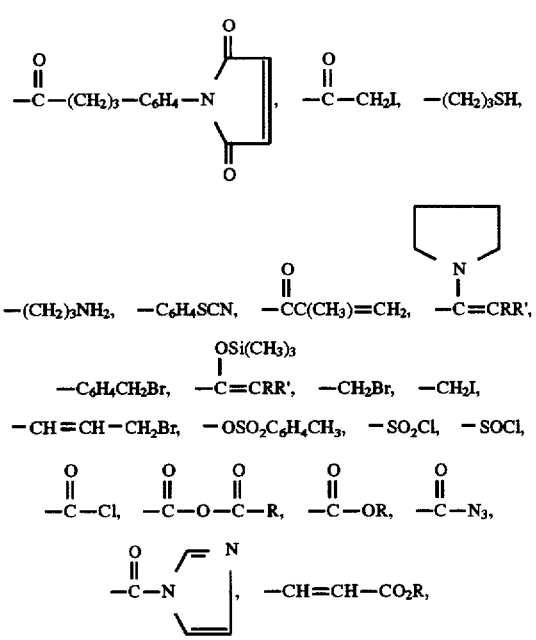

and R and R' are the same or different and each stands for a hydrogen atom, a saturated or unsaturated $C_1$–$C_{20}$ hydrocarbyl, e.g., aliphatic, e.g., alkyl, radical optionally substituted by a phenyl group, or a phenyl group.

As examples for the complexing radicals K there can be mentioned those of ethylenediaminetetraacetic acid, diethylenetraiaminepentaacetic acid, trans-1,2-cyclohexanediaminotetraacetic acid, 1,4,7,10-tetraazacylcododecanetetraacetic acid, 1,4,7-triazacyclononanetriacetic acid, 1,4,8,11-tetraazatetradecanetetraacetic acid and 1,5,9-triazacyclododecanetriacetic acid, which by (in each case contained in K) a carbon atom or a carbonyl group are bonded on the radicals of the polymer unit. In all cases, a part of the carboxylic acid groups can be present as ester and/or amide groups.

As polymers suitable for production of the polymer complexes according to the invention there can be mentioned, for example, polyethylenimine, polylysine, polyasparaginic acid, polyethyleniminopolyacetic acid ester or polyacryl ester.

The remaining acid hydrogen atoms, i.e., those which were not substituted by the central ion, can optionally be replaced, wholly or partly, by cations of inorganic and/or organic bases of amino acids. The corresponding acid groups can also be converted partly or wholly to esters or amides.

Suitable inorganic cations are, for example, the lithium ion, the calcium ion and especially the sodium ion. Suitable cations of organic bases are, among others, those of primary, secondary and tertiary amines, such as, e.g., ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acidic or neutral amino acids. Suitable esters are preferably those with a $C_1$–$C_6$ alkyl radical; there can be mentioned, for example, the methyl, ethyl and tert-butyl radical. If the carboxylic acid groups are to be present at least partly as amides, then tertiary amides are preferred. Saturated, unsaturated, straight-chain or branched-chain or cyclic hydrocarbons with up to 5 C atoms, which optionally are substituted by 1 to 3 hydroxy or $C_1$–$C_4$ alkoxy groups, are suitable as radicals. There can be mentioned, for example: the methyl, ethyl, 2-hydroxyethyl, 2-hydroxy-1-(hydroxymethyl)-ethyl, 1-(hydroxymethyl)-ethyl, propyl, isopropenyl, 2-hydroxypropyl, 3-hydroxypropyl, 2,3-dihydroxypropyl, butyl, isobutyl, isobutenyl, 2-hydroxybutyl, 3-hydroxybutyl, 4-hydroxybutyl, 2-, 3- and 4-hydroxy-2-methybutyl, 2- and 3-hydroxyisobutyl, 2,3,4-trihydroxybutyl, 1,2,4-trihydroxybutyl, pentyl, cyclopentyl and 2-methoxyethyl group. The amide radical can also be a heterocyclic 5- or 6-member ring formed by inclusion of the amide nitrogen. For example, there can be mentioned: pyrrolidinyl, piperidyl, pyrazolidinyl, pyrrolinyl, pyrazolinyl, piperazinyl, morpholinyl, imidazolidinyl, oxazolidinyl, or thiazolidinyl rings.

The polymer complexes according to the invention can contain a great number of metal ions, stably bonded in the complex, necessary for their use.

Thus, e.g., equilibrium and recomplexing investigations with the gadolinium complex of diethylenetriaminepentaacetic acid DTPA (European specification EP 71 564), recognized by experts as a good prior art contrast medium, show that the polymer complexes according to the invention in a surprising way are more stable than Gd-DTPA is over the entire molecular range (5–2000 kD) determined by the foregoing index numbers.

Also the compatibility of the polymer complexes is, for example, superior to the organ-specific monomer complexes.

The value for the magnitude of the relaxivity representing a measurement of the imaging is surprisingly high; it is higher by a factor of 3–1000 for the polymer complexes according to the invention than for gadolinium DTPA. As a result, to maintain a specific signal strength with the imaging, a correspondingly smaller molar amount of complex in comparison with the monomers is necessary.

As another important advantage of the polymer complexes according to the invention, their excretion behavior can be mentioned. The desired excretion rate depending on the purpose of use can be set very specifically and simply by the molecular weight to be selected, i.e., in general, the higher the molecular weight the slower and more incomplete is the excretion.

The polymer complexes according to the invention exhibit a surprisingly high tissue specificity. Thus, for example, already a few minutes after intravenous injection of an N-methylglyucamine salt solution of gadolinium(III) complex of the polyethyleninime poly-DTPA (see example 1), in the nuclear magnetic image a marked contrast enhancement is obtained in the peripheral tumor tissue, which lasts for a prolonged period and brings a marked diagnostic gain.

Surprisingly, with the help of the polymer complexes according to the invention blood vessels can be represented in vivo without use of special pulse sequences, so that, among other things, they can be used as perfusion agents.

The production of the polymers according to the invention can be achieved by conventional processes wherein polymers provided with amino, imino and/or

subunits, in which Fl stands for a leaving group, are converted by alkylation, acylation, amidation and/or hydrazination into compounds which exhibit as polymer units structures of general formula I'

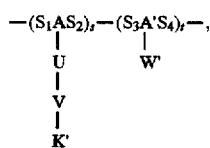     (I')

in which

A, A', U, V, $S_1$, $S_2$, $S_3$, $S_4$, s and t have the meanings indicated above and K' are complexing agents of general formula IA', IB', IC' and ID' which are identical with the formulas indicated for IA, IB, IC and ID, but, instead of the substituents X and Z, each carries X' and Z", and X', independently of one another, stand for —COOH and Z" stands for the group

or the radical X',
and wherein optionally a part of the COOH groups is present as ester and/or amide, W' means a hydrogen atom, the group $U_w$—$V_w$—$K'_w$ ($U_w$ and $V_w$ have the meaning named above and $K'_w$ has the meaning named for K), V' or the group

and V'" stands for the radical V having a functional group on the end, then, in a way known in the art, these are optionally reacted with at least one metal oxide or metal salt of an element of atomic numbers 21–29, 42, 44 or 57–83, and optionally K' and/or W' by conversion of at least one of —$CO_2H$ groups contained in K' or W' into the desired alkylene group having a functional group on the end and optionally subsequent linkage with a macromolecule or biomolecule and/or by bonding on the biotin radical or avidin radical are converted into K and W, and said reaction steps (except for the macromolecule or biomolecule linkage, which can take place only after generation of the functional group) can be performed in any sequence, and optionally then the acid hydrogen atoms still present in the obtained polymer complexes can be substituted wholly or partly by cations of inorganic and/or organic bases, amino acids or amino acid amides or the corresponding acid groups can be converted wholly or partly into esters or amides.

The processes can begin with polymers such as, e.g., polyethylenimine, polyethylenimine polyacetic acid derivatives, polyacrylester or polylysine, which optionally contain

groups, in which Fl stands for a leaving group as, for example, Cl, Br, I, $NH_2$, $OCH_3$, $OC_2H_5$, $OCH_2C_6H_5$, $OC_3H_7$, mesylate or tosylate.

These compounds, in a way known in the art, are amidated, hydrazinated (Houben-Weyl, Methoden der organischen Chemie [Methods of Organic Chemistry], Volume VIII/3 Georg Thieme Verlag, Stuttgart (1952), 654 and 676), acylated (J. March, Advanced Organic Chemistry, McGraw-Hill, 2nd ed., (1977) 377–382) and/or alkylated (Houben-Weyl, Methoden der organischen Chemie, Volume VI/3 Georg Thieme Verlag, Stuttgart (1965), 187).

As substrates for introduction of the complexing units K—V or $K_w$—$V_w$, compounds of general formulas I'A, I'B, I'C,I'D, I"A,B and I"C are used

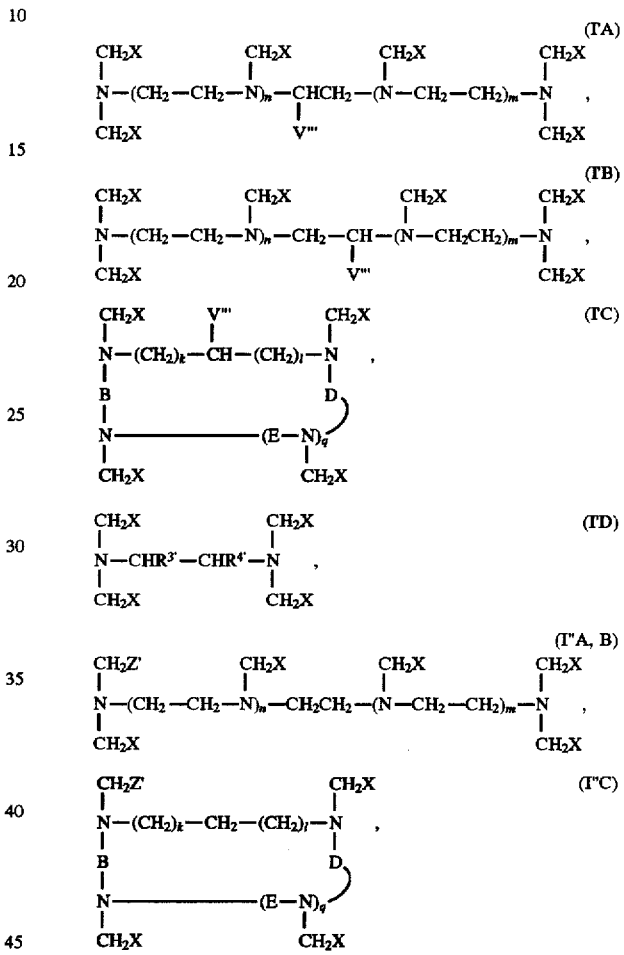

in which V'" stands for a substituent to be converted into V or V", $R^{3'}$ and $R^{4'}$ stand for $R^3$ and $R^4$, which contain the substituent V'", and Z' stands for an activated carbonyl group.

As example of an activated carbonyl group there can be mentioned anhydride, p-nitrophenyl ester and acid chloride.

The alkylation or acylation performed for introduction of the complexing units is performed with reagents, which contain the desired K—V or $K_w$—$V_w$ substituent (bonded on a leaving group) or from which the desired substituent, optionally after modification by secondary reaction(s), is generated by the reaction. As examples for the first named there can be mentioned halides, mestylates, tosylates and anhydrides. To the second group there belong, for example, oxiranes, thiiranes, aziranes, alpha,beta-unsaturated carbonyl compounds or their vinylogs, aldehydes, ketones, isothiocyanates or isocynates.

As examples for secondary reactions there can be mentioned ester cleavages, hydrogenations, esterifications, oxidations, etherifications and alkylations, which are performed according to the literature processes known to one skilled in the art.

Compounds of I' needed as feedstock are known (e.g., European patent application publication No. 0154788) or can be produced from the corresponding polyamines (and functional groups present optionally are protected) by alkylation with an ester of general formula II

in which Hal stands for chlorine, bromine or iodine and Y stands for an acid protecting group.

The reaction takes place in polar aprotic solvents such as, for example, dimethyl formamide, dimethyl sulfoxide or hexamethylphosphoric acid triamide in the presence of an acid trap, such as, for example, of tertiary amine (for example, triethylamine, trimethylamine, N,N-dimethylaminopyridine, 1,5-diazabicyclo[4.3.0]none-5 (DBN), 1,5-diazabicyclo[5.4.0]undecene-5-DBU), alkali and alkaline earth carbonate or bicarbonate (e.g., sodium, magnesium, calcium, barium, potassium carbonate and bicarbonate) at temperatures between −10° C. and 120° C., preferably between 0° C. and 50° C.

Suitable as acid protecting groups Y are lower alkyl, aryl and aralkyl groups, for example, methyl, ethyl, propyl, butyl, phenyl, benzyl, diphenylmethyl, triphenylmethyl, bis-(p-nitrophenyl)-methyl group, as well as trialkylsilyl groups.

Cleavage of protecting groups Y takes place according to processes known to one skilled in the art, for example, by hydrolysis, alkaline saponification of the esters with alkali in aqueous alcoholic solution at temperatures of 0° C. to 50° C. or in case of tert-butyl esters with the help of trifluoroacetic acid.

The production of the activated carbonyl derivatives I" (e.g., mixed anhydride, N-hydroxysuccinimide ester, acylimidazoles, trimethylsiyl ester) takes place according to methods known in the literature (Houben-Weyl, Methoden der organischen Chemie [Methods of Organic Chemistry] Georg Thieme Verlag, Stuttgart, volume E 5(1985), 633; Org. React. 12, 157(1962)] or as will be described in the experimental part.

The corresponding polyamines necessary as feedstock for the production of polyamine polyacids of general formula I'A are produced analogously to methods known in the literature (for example, Canad. Patent No. 1 178 951, Eur. I. Med. Chem. Chim. Ther. 1985, 20, 509 and 1986, 21, 333), by starting from amino acids which are converted into optionally ethylene amine substituted amides (for example, with N-(2-aminoethyl)-carbamine acid benzyl ester) and then (optionally after cleavage of the protecting groups) are reduced to the desired amines (preferably with diborane or lithium aluminum hydride).

If it is desired to synthesize the polyamime feedstocks for the compounds of general I'B, it is necessary before reduction to substitute such an amide on the alpha amino group by reaction with, for example, ethyloxamate in a polar solvent such as, for example, tetrahydrofuran, dimethyl sulfoxide or dimethoxyethane at a temperature between 50° C. and 250° C., preferably 70° C. to 150° C. (optionally in a pressure vessel) so that a 3-aza-2-oxo-glutaric acid diamide derivative is obtained as intermediate product.

The production of the cyclic polyamines necessary as feedstock for I'C or I"C takes place by ring formation of two reactants, of which (in case of synthesis of I'C) the one is V'"-substituted.

The ring formation is performed according to methods known in the literature, for example, Org. Synth. 58,86 (1978), Macrocyclic Polyether Synthesis, Springer Verlag, Berlin, Heidelberg, N.Y. 1982, Coor. Chem. Rev. 3,3 (1968), Ann. Chem. 1976, 916: one of the two reactants carries on the chain end two leaving groups, the other carries two nitrogen atoms, which nucleophilically displace these leaving groups. As an example there can be mentioned the reaction of terminal dibromo, dimesyloxy, ditosyloxy or dialkoxy carbonylalkylene compounds optionally containing one or two nitrogen atom(s) with terminal diazaalkylene compounds—of which (in case of synthesis of I'C) one of the two reactants is V'"-substituted—optionally containing one or two additional nitrogen atom(s) in the alkylene chain.

The nitrogen atoms are optionally protected, for example as tosylates, and are set free before the subsequent alkylating reaction according to methods known in the literature.

If diesters are used in the ring formation reaction, the diketo compounds thus obtained must be reduced by process (s) know to one skilled in the art, for example, with diborane.

As substituent V'", which can be converted into V or into the substituent V" exhibiting on the end a functional group suitable for a bond on a macromolecule or biomolecule, there are suitable, among others, hydroxy and nitrobenzyl, hydroxy and carboxyalkyl as well as thioalkyl radicals with up to 20 carbon atoms. They are converted according to the process in the literature known to one skilled in the art (Chem. Pharm. Bull. 33,674 (1986), Compendium of Org. Synthesis Vol. 1–5, Wiley and Sons, Inc., Houben-Weyl, Methoden der organischen Chemie, Volume VIII, Georg Thieme Verlag, Stuttgart, J. Biochem. 92, 1413, 1982) into the desired substituents (for example, with the amino, hydrazino, hydrazinocarbonyl, epoxide, anhydride, methacryloylhydrazinocarbonyl, maleimidamidocarbonyl, halo, halocarbonyl, mercapto, isothiocyanate group as functional group), and in case of the nitrobenzyl radical first a catalytic hydrogenation (for example, according to P. N. Rylander, Catalytic Hydrogenation over Platinum Metals, Academic Press 1967) to the aminobenzyl derivative must be performed.

Examples for the conversion of hydroxy or amino groups bonded on aromatic or aliphatic radicals are the reactions performed in anhydrous, aprotic solvents such as tetrahydrofuran, dimethoxyethane or dimethyl sulfoxide in the presence of an acid trap such as, for example, sodium hydroxide, sodium hydride or alkaline or alkaline earth carbonates such as, for example, sodium, magnesium, potassium, calcium carbonate at temperatures between 0° C. and the boiling point of the respective solvent, but preferably between 20° C. and 60° C., reactions performed with a substrate of general formula III

in which Nf stands for a nucleofuge such as, e.g., Cl, Br, I, $CH_3C_6H_4SO_3$ or $CF_3SO_3$, L stands for an aliphatic, aromatic, arylaliphatic, branched, straight-chain or cyclic hydrocarbon radical with up to 20 carbon atoms and Fu stands for the desired terminal functional group, optionally in protected form (DE-OS 34 17 413).

As examples for compounds of general formula III there can be mentioned
$Br(CH_2)_2NH_2$, $Br(CH_2)_3OH$, $BrCH_2COOCH_3$, $BrCH_2CO_2^tBu$, $ClCH_2CONHNH_2$, $Br(CH_2)_4CO_2C_2H_5$, $BrCH_2COBr$, $BrCH_2CONH_2$, $ClCH_2COOC_2H_5$, $BrCH_2CONHNH_2$,

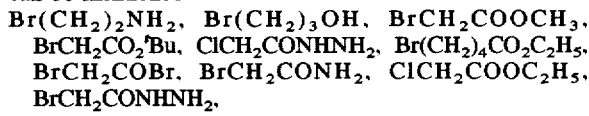

$CF_3SO_3(CH_2)_3Br$, $BrCH_2C\equiv CH$, $BrCH_2CH=CH_2$.

Conversions of carboxy groups can be performed, for example, according to the carbodiimide method (Fieser, Reagents for Organic Synthesis 10, 142) by a mixed anhydride [Org. Prep. Proc. Int. 7,215 (1975)] or by an activated ester (Adv. Org. Chem. Part B, 472).

The production of the amines necessary as initial substances for ring formation takes place analogously to methods known in the literature.

Starting from an N-protected amino acid there are obtained by reaction with a partly protected diamine (for example, according to the carbodiimide-method) cleavage of the protecting groups and by diborane reduction a triamine.

The reaction of a diamine obtainable from amino acids (Eur. J. Med. Chem.-Chim. Ther. 21, 333 (1986) with a double molar amount of an N-protected omega-amino acid yields a tetramine after suitable working up.

In both cases the number of carbon atoms between the N atoms can be determined by the kind of diamines or amino acids used as coupling participants.

A part of the acid groups of the polymer compounds thus obtained introduced by complexing units K or $K_w$ can optionally be further functionalized by the process known to one skilled in the art, for example, by conversion into ester, amide, hydrazide, maleimido or other groups, which are suitable for coupling on biomolecules or macromolecules.

The complexing ligands (as well as the complexes) thus obtained can also be attached on biomolecules or macromolecules, of which it is known that they concentrate in the organ or organ part to be examined. Such molecules are, for example, enzymes, hormones, dextrans, porphyrins, bleomycins, insulin, prostaglandins, steroid hormones, amino sugars, amino acids, peptides such as polylysine, proteins (such as, for example, immunoglobulins, monoclonal antibodies, lectins) or lipids (also in the form of liposomes). Especially to be stressed are conjugates with albumins, such as human serum albumin, antibodies, such as, for example, monoclonal, for tumor-associated antigens specific for antibodies and antimyosin. Instead of biological macromolecules, suitable synthetic polymers such as polyethylenimines, polyamides, polyureas, polyethers and polythioureas can be attached. The pharmaceutical agents formed therefrom are suitable, for example, for use in tumor and infarct diagnosis as well as tumor therapy. Monoclonal antibodies (for example, Nature 256, 495, 1975), in comparison with polyclonal antibodies, have the advantages that they are specific for an antigen determinant, have a defined bonding affinity, are homogeneous (thus their preparation in a pure condition becomes basically simpler) and can be produced in cell cultures in large amounts. As such, for example for visualization of tumors, monoclonal antibodies or their fragments Fab and F(ab')$_2$ are suitable, which, for example, are specific for human tumors of the gastrointestinal tract, breast, liver, bladder, gonads and of melanoma (Cancer Treatment Repts. 68, 317, 1984, Bio. Sci. 34, 150, 1984) or against carcinoembryonal antigen (CEA), human choriogonadotrophin (beta-HCG) or other tumor-fixed antigens, such as glycoproteins (New Engl. J. Med. 298, 1384, 1973, U.S. Pat. No. 4,331,647). Also suitable, among others, are antimyosin, anti-insulin antibody and antifibrin antibodies (U.S. Pat. No. 4,036,945).

Colon carcinomas can he detected by NMR diagnosis with the help of polyethylenimine poly-DTPA polyhydrazide conjugates complexed with gadolinum(III) ions with antibody 17-1A (Centocor, U.S.A).

For liver examinations or tumor diagnosis, conjugates or inclusion compounds with liposomes, for example, are suitable, which, for example, are used as unilamellar or multilamellar phosphatidylcholine cholesterol vesicles.

The bonding of metals on the desired macromolecules or bimolecules occurs according to methods, such as described, for example, in Rev. Roum. Morphol. Embryol. Physio., Physiologie 1981, 18, 241 and J. Pharm. Sci. 68, 79 (1979), for example, by reaction of the nucleophilic group of a macromolecule, such as an amino, phenol, sulfhydryl, aldehyde or imidazole group with an activated derivative of the polymer complex or ligand. Suitable as activated derivatives are, for example, anhydrides, acid chlorides, mixed anhydrides (see, for example, G. E. Krejcarek and K. L. Tucker, Biochem., Biophys. Res. Commun. 1977, 581), activated esters, nitrenes or isothiocyanates. Conversely, it is also possible to react an activated macromolecule with the polymer complex or ligand. For conjugation with proteins, substituents are also available, for example, of the structure $C_6H_4N_2^+$, $C_6H_4NHCOCH_2$, $C_6H_4NCS$ or $C_6H_4OCH_2CO$.

However, this type of bonding is subject to the drawback of a deficient complex stability of the conjugates or deficient specificity (for example, Diagnostic Imaging 84, 58; Science 220, 613, 1983; Cancer Drug Delivery 1, 125, 1984). On the other hand, the conjugate formation according to the present invention takes place by functional groups in K and/or W. As a result, up to several hundred metal ions can be bonded by one bonding site.

In case of antibody conjugates the bonding of the antibodies on the complex or ligand should not lead to the loss or reduction of the bonding affinity and bonding specificity of the antibody for the antigen. This can take place either by bonding on the carbohydrate portion in the Fc part of the glycoprotein or in the Fab or F(ab')$_2$ fragments or by bonding on sulfur atoms of the antibody or the antibody fragments.

In the first case, an oxidative cleavage of sugar units is first performed for generation of formyl groups that can be coupled. This oxidation can be performed chemically with oxidizing agents such as, e.g., periodic acid, sodium metaperiodate and potassium metaperiodate according to methods known in the literature (for example, J. Histochem and Cytochem. 22, 1084, 1974) in aqueous solution in concentrations of 1 to 100, preferably 1 to 20 mg/ml, and a concentration of the oxidizing agent between 0.001 to 10 mmol, preferably 1 to 10 mmol in a pH range of about 4 to 8 at a temperature between 0° and 37° C. and a reaction time between 15 minutes and 24 hours. The oxidation can also be performed enzymatically, for example, with the help of galactose oxidase in an enzyme concentration of 10–100 units/ml, a substrate concentration of 1 to 20 mg/ml, at a pH of 5 to 8, a reaction time of 1 to 8 hours and a temperature between 20° and 40° C. (for example, J. Biol. Chem. 234, 445, 1959).

By the oxidation of the generated aldehydes, complexes or ligands are bonded with suitable functional groups such as, for example, hydrazine, hydrazide, hydroxylamine, phenylhydrazine, semicarbazide and thiosemicarbazide by reaction between 0° and 37° C., at a reaction time of 1 to 65 hours, a pH between about 5.5 and 8, an antibody concentration of 0.5 to 20 mg/ml and a molar ratio of complexing agent to antibody aldehyde of 1:1 to 1000:1. The subsequent stabilization of the conjugate takes place by reduction of the double bond, e.g., with sodium borohydride or sodium cyanoborohydride; the reducing agent in this case is used in a 10 to 100 time excess (for example, J. Biol. Chem 254, 4359, 1979).

The second possibility of formation of antibody conjugates starts from a gentle reduction of the disulfide bridges of the immunoglobulin molecule; as a result the more sensitive disulfide bridges between the H chains of the antibody molecule are cleaved, while the S—S bonds of the antigen-bonding region remain intact, so that practically no reduction of the bonding affinity and specificity of the antibody occurs (Biochem. 18, 2226, 1979, Handbook of Experimental Immunology, Vol. 1, Second Edition, Blackwell Scientific Publications, London 1973, Chapter 10). These free sulfhydryl groups of the inter-H-chain regions are then reacted with suitable functional groups of complexing agents or metal complexes at 0° to 37° C., a pH of about 4 to 7, and a reaction time of 3 to 72 hours to form a covalent bond, which does not adversely affect the antigen bond region of the antibody. As suitable reactive groups there can be mentioned for example: haloalkyl, haloacetyl, p-mercuric benzoate groups as well as groups which are subjected to a Michael addition reaction such as, for example, maleinimides and methacrylo groups (for example, J. Amer. Chem. Soc. 101, 3097, 1979).

For linking the antibody fragments to the polymer complexes or the ligands, there is an additional series of suitable, often also commercially available, bifunctional "linkers" (see, for example, Pierce, Handbook and General Catalogue 1986), which are reactive to both the SH groups of the fragments and to the amino or hydrazino groups of the polymers.

As examples there can be mentioned:
m-maleimidobenzoyl-N-hydroxysuccinimide ester (MBS),
m-maleimidobenzoyl-N-sulfosuccinimide ester (Sulfo-MBS),
N-succinimidyl-[4-(iodoacetyl)-amino]benzoic acid ester (SIAB),
succinimidyl-4(N-maleimidomethyl)-cyclohexane-1-carboxylic acid ester (SMCC),
succinimidyl-4(p-maleimidophenyl)-butyric acid ester (SMPB),
N-succinimidyl-3-(2-pyridyldithio)-propionic acid ester (SDPD),
4-[3-(2,5-dioxo-3-pyrrolinyl)-propinyloxy]-3-oxo-2,5-diphenyl-2,3-dihydrothiophene-1,1-dioxide.

Noncovalent type bonds can also be used for coupling, and both ionic and van der Waals and hydrogen bridge bonds in varying portions and strengths (key-lock principle) can contribute to the bond (for example, avidin-biotin, antibody-antigen). Also inclusion compounds (host-guest) of smaller complexes in the larger cavities of the macromolecule are possible.

The coupling principle consists first in producing a bifunctional macromolecule, by either an antibody hybridome, directed against a tumor antigen being fused with a second antibody hybridome directed against a complex according to the invention or the two antibodies being chemically linked to one another by a linker (for example, in the way indicated in J. Amer. Chem. Soc. 101, 3097 (1979)) or the antibody directed against the tumor antigen, optionally by a linker, being bonded on avidin (or biotin) [D. J. Hnatowich et al., J. Nucl. Med. 28, 1294 (1987)]. Instead of the antibodies their corresponding F(ab) or F(ab')$_2$ fragments can be used. For pharmaceutical use, first the bifunctional macromolecule is injected, which accumulates on the target site, and then in the time interval the complex compound according to the invention [optionally is bonded on biotin (or avidin)] is coupled in vivo on the target site and there can develop its diagnostic or therapeutic action. Moreover, other coupling methods can also be used, such as, for example, the "Reversible Radiolabeling" described in Protein Tailoring Food Med. Uses [Am. Chem. Soc. Symp. (1985), 349].

An especially simple method for the production of antibody conjugates or antibody fragment conjugates is available with the so-called solid phase coupling: the antibody is coupled on a stationary phase (e.g., an ion exchanger), which, for example, is in a glass column. Very high conjugate yields are obtained by successive flushing of the column with a solution suitable for generation of aldehyde groups, washing, flushing with a solution of the functionalized complex (or ligand), washing (if the ligand is used, another flushing takes place with a solution containing the metal salt, followed by several rinsings) and finally eluting of the conjugate.

This process allows the automatic and continuous production of any amounts of conjugates.

Other coupling steps can also be performed in this way.

Thus, a preferred process for the production of polymer complexes is one wherein the coupling of the macromolecule or biomolecule on the functionalized polymer complex or ligand as well as, in case of coupling on the ligand, the subsequent complexing with the desired metal ion(s) is performed on a stationary phase.

Thus, for example, fragment conjugates can be produced by the sequence papain reduction/bifunctional linker/functionalized complex or ligand.

The compounds thus formed are then preferably purified chromatographically over ion exchangers on a fast protein liquid chromatography unit.

Production of the metal complexes according to the invention takes place in the way disclosed in specification DE-OS 34.01.052 in that the metal oxide or a metal salt (for example, the nitrate, acetate, carbonate, chloride or sulfate of the element of atomic numbers 21–29, 42, 44, 57–83) is dissolved or suspended in water and/or a lower alcohol (such as methanol, ethanol or isopropanol) and reacted with a solution or suspension of the equivalent amount of the complexing ligand and then, if desired, present acid hydrogen atoms of the acid or phenol groups are substituted by cations of inorganic and/or organic bases or amino acids.

In this case, neutralization takes place with the help of inorganic bases (for example, hydroxides, carbonates or bicarbonates) of, for example, sodium, potassium, lithium, magnesium or calcium and/or organic bases such as, among others, primary, secondary and tertiary amines such as, e.g., ethanolamine, morpholine, glucamine, N-methyl and N,N-dimethylglucamine, as well as basic amino acids, such as, for example, lysine, arginine and ornithine or of amides of originally neutral or acidic amino acids.

For production of neutral complex compounds, a sufficient amount of the desired base(s) can be added to the acid complex salts in aqueous solution or suspension so that the neutral point is reached. The resulting solution can then be concentrated by evaporation in a vacuum to dryness. It is often advantageous to precipitate the formed neutral salts by addition of water-miscible solvents, such as, for example, lower alcohols (methanol, ethanol, isopropanol and others), lower ketones (acetone and others), polar ethers (tetrahydrofuran, dioxane, 1,2-dimethoxyethane and others) and to obtain crystallizates easy to isolate and purify. It has proved especially advantageous to add the desired base during complexing of the reaction mixture and thus to save a process step.

If the acid complex compounds contain several free acid groups, it is often suitable to produce neutral mixed salts, which contain both inorganic and organic cations and counterions.

This can happen, for example, in that the complexing ligand is reacted in aqueous suspension or solution with the oxide or salt of the element yielding the central ion and half of the amount of an organic base necessary for the neutralization. The formed complex salt is isolated, optionally purified, and then is mixed until complete neutralization with the necessary amounted of inorganic base. The sequence of addition of bases can also be reversed.

Another possibility to arrive at the neutral complex compounds consists in converting the remaining acid groups in the complex completely or partly, for example, to esters or amides. This can take place by subsequent reaction on the finished polymer complex (e.g., by exhaustive reaction of the free carboxy groups with dimethyl sulfate) as well as by use of a suitably derivatized substrate for introduction of the complexing units K—V or $K_w$—$V_w$ of general formulas I'A, I'B, I'C, I'D, I"A,B, I"C (e.g., $N^3$-(2,6-dioxomorpholinomethyl)-$N^6$-(ethoxycarbonylmethyl)-3,6-diazaoctanedioic acid).

The conjugates of antibody and complex, before in vivo use, after incubation, are dialyzed with a weak complexing agent, such as, for example, sodium citrate, sodium ethylene diaminetetraacetic acid, to remove weakly bonded metal atoms.

The production of the pharmaceutical agents according to the invention also takes place in a way known in the art, in that the complexing compounds according to the invention—optionally with addition of the additives usual in galenicals—are suspended or dissolved in an aqueous medium and then the suspension or solution is optionally sterilized. Suitable additives are, for example, physiologically compatible buffers (such as, for example, tromethamine), slight additives of complexing agents (such as, for example, diethylenetriaminepentaacetic acid) or, if necessary, electrolytes such as, for example, sodium chloride or, if necessary, antioxidants such as, for example, ascorbic acid.

If suspensions or solutions of agents according to the invention in water or physiologically saline solution are desired for enteral administration or other purposes, they are mixed with one or more auxiliary agent(s) conventional in galenicals (for example, methylcellulose, lactose, mannitol) and/or surfactants) (for example, lecithins, Tween®, Myrj® and/or aromatic substances) for flavoring (e.g., essential oils).

In principle, it is also possible to produce the pharmaceutical agents according to the invention without isolation of the complex salts. But, in every case special care must be taken to perform the chelate formation so that salts and salt solutions according to the invention are practically free of uncomplexed toxically acting metal ions.

This can be guaranteed, for example, with the help of color indicators such as xylenol orange, by controlled titration during the production process. Therefore, the invention also relates to processes for the production of complex compounds and their salts. As a last safety measure there remains a purification of the isolated complex salt.

The pharmaceutical agents according to the invention preferably contain 1 micromol-1 mol/l of the metal in the form of its complex salt and as a rule is dosed in amounts of 0.001–5 mmol metal/kg of body weight. They are intended for enteral and parenteral application.

The agents according to the invention meet the diverse requirements for suitability as contrast media for nuclear magnetic resonance imaging or MRI (nuclear spin tomography). They are outstandingly suitable, after oral or parenteral application, for improving the image obtained with the help of the nuclear spin tomograph in its expressiveness by enhancement of the signal intensity. Further, they exhibit the high effectiveness, which is necessary, to load the body with the smallest possible amounts of foreign substances and the good compatibility, which is necessary, to maintain the noninvasive character of the examinations.

The good water solubility of the media according to the invention makes it possible to produce highly concentrated solutions to keep the volume load of the circulation within tolerable limits and to balance the thinning by body fluids, i.e., NMR diagnostic media must be 100 to 1000 times more water soluble than for NMR spectroscopy. Further, the media according to the invention exhibit not only a high in vitro stability but also a surprisingly high in vivo stability, so that a release or an exchange of the ions not covalently bonded in the complexes—ions that are toxic per se—takes place only extremely slowly within the time it takes the new contrast media to be completely eliminated.

In general the media according to the invention for use as NMR diagnostic media are dosed in amounts of 0.001–5 mmol metal/kg of body weight, preferably 0.005–0.5 mmol metal/kg of body weight. Details of the use are discussed, for example, in H. J. Weinmann et al., Am. J. of Roentgenology 142, 691 (1984). Especially low dosages (under 1 mg/kg of body weight) of organ-specific NMR diagnostic agents can be used, for example, for detection of tumors and myocardial infarct. Further, the complex compounds are advantageously used as shift and susceptibility reagents.

The media according to the invention are also suitable as X-ray contrast media, and it is to be especially stressed that they, in comparison with iodine-containing contrast media used up to now, exhibit pharmacokinetics substantially more favorable for diagnosis. Further, they are especially valuable because of the favorable absorption properties in the regions of higher anode voltages for digital subtraction techniques. In general, for use as X-ray contrast media, the media according to the invention are dosed analogously to the example of meglumine diatrizoate in amounts of 0.1–5 mmol of metal/kg of body weight, preferably 0.25–1 mmol of metal/kg of body weight.

Details of the use of X-ray contrast media are, for example, discussed in Barke, Roentgenkontrastmittel [X-Ray Contrast Media], G. Thieme, Leipzig (1970) and P. Thurn, E. Buecheler—"Einfuehrung in die Roentgendiagnostik" [Introduction to X-Ray Diagnosis], G. Thieme, Stuttgart, N.Y. (1977).

The media according to the invention—since their acoustic impedance is higher than that of body fluids and tissues—are also suitable as contrast media for ultrasonic diagnosis, especially in the form of suspensions. They are generally dosed in amounts of 0.1–5 mmol/kg of body weight, preferably 0.25–1 mmol/kg of body weight.

Details of the use of ultrasonic diagnostic agents are described, for example, in T. B. Tyler et al., Ultrasonic Imaging 3.323 (1981), J. I. Haft, "Clinical Echokardiography," Futura, Mount Kisco, N.Y. 1978 and G. Stefan "Echokardiaographie" [Echocardiography], G. Thieme Stuttgart/N.Y. 1981.

Altogether, there has been success in synthesizing new polymer complexes, which open up new possibilities in diagnostic and therapeutic medicine. Especially the development of new types of imaging processes in medical diagnosis makes this development desirable.

The polymer complexes containing polymer units of general formula I' can also be used as haptens for production of antibodies. Details of the use of haptens for production of antibodies are described, e.g., in S. Sell, Immunology, Immunopathology and Immunity, 372, Harper and Row Publ., 3rd ed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents and publications cited above and below, and of West German Application P 38 06 795 of Feb. 29, 1988, are hereby incorporated by reference.

EXAMPLE 1 a) O-benzyl-N-trifluoroacetyltyrosine 112.5 g (0.41 mmol) of O-benzyltyrosine is suspended in 1 liter of dry methanol and mixed at room temperature with 58.9 ml (0.42 mol) of triethylamine. After addition of 67 ml (0.53 mol) of trifluoroacetic acid methyl ester, it is stirred for 130 hours at room temperature with exclusion of water. The unreacted initial material is separated and the leaving components are removed by shaking with ethyl acetate/aqueous hydrochloric acid. The ethyl acetate phase is decolored with activated carbon. After evaporation of the solvent, 120.7 g (80% of theory) of colorless crystals is obtained.

Melting point: 149°–150° C.

| Analysis | | | | | |
|---|---|---|---|---|---|
| Cld: | C 58.85 | H 4.39 | N 3.81 | O 17.42 | F 15.51 |
| Fnd: | C 58.78 | H 4.29 | N 3.79 | | F 15.57 | b) O-benzyl-N-trifluoroacetyltyrosine-(2-carbobenzoxyaminoethylene)amide 18.5 g (50.4 mmol) of O-benzyl-N-trifluoroacetyltyrosine (example 1a) is dissolved in 200 ml of dry tetrahydrofuran, mixed with 7 ml of triethylamine and then 4.8 ml (50.8 mmol) of chloroformic acid ethyl ester is added by instillation, and the temperature is kept below −10° C. After completion of the addition, it is stirred for 30 minutes at this temperature, again mixed with the same amount of precooled triethylamine and an ice-cold solution of 11.6 g (50.4 mmol) of N-(2-aminoethyl)-carbamic acid benzyl ester hydrochloride in 100 ml of dimethylformamide is instilled. It is stirred for 30 minutes more at −10° C., then allowed to come to room temperature with stirring and then warmed for 10 minutes to 30° C. Then the solvent is removed on a rotation evaporator and pouring on 750 ml of ice water is performed. The crystallizate is suctioned off, washed with ice water and dried. The yield is 26.9 g (94% of theory).

Melting point: 189°–190° C.

| Analysis | | | | | |
|---|---|---|---|---|---|
| Cld: | C 61.87 | H 5.19 | N 7.73 | O 14.71 | F 10.48 |
| Fnd: | C 61.90 | H 5.08 | N 7.77 | | F 10.43 | c) O-benzyltyrosine-(2-carbobenzoxyaminoethylene)amide 25.9 g (47.8 mmol) of O-benzyl-N-trifluoroacetyltyrosine-(2-carbobenzoxyaminoethylene) amide (example 1b) is suspended in 300 ml of ethanol and mixed by portions with 7.2 g (191 mmol) of sodium borohydride. After stirring overnight at room temperature, it is mixed with 50 ml of acetone, freed of solvent, mixed with 500 ml of water and extracted several times with ethyl acetate. The organic phase yields, after drying and concentration by evaporation, 18.8 g (88% of theory) of white crystals with a melting point of 145° C.

| Analysis | | | | |
|---|---|---|---|---|
| Cld: | C 69.77 | H 6.53 | N 9.38 | O 14.29 |
| Fnd: | C 69.79 | H 6.53 | N 9.35 | | d) Tyrosine-(2-aminoethylene)amide 42.3 g (94.6 mmol) of the compound according to example 1c is dissolved in 1.1 liter of methanol, 2 g of 10% palladium carbon is added and hydrogenated with stirring until no further hydrogen absorption takes place. The catalyst is filtered off and the solvent is evaporated. It is dissolved in heat in methanol and precipitated with ether. 17 g (86% of theory) of colorless crystals is obtained.

Melting point: 138°–141° C.

| Analysis | | | | |
|---|---|---|---|---|
| Cld: | C 59.17 | H 7.67 | N 18.81 | O 14.33 |
| Fnd: | 59.23 | H 7.51 | N 18.90 | | e) 3-Aza-1-(4-hydroxybenzyl)-pentane-1,5-diamine trihydrochloride 6.55 g (29.3 mmol) of the compound according to example 1d is suspended in 130 ml of dry tetrahydrofuran and a slow current of diborane (of 5.8 g of sodium borohydride in 75 ml of diethyleneglycodimethyl ether and 54 ml of boron trifluoride etherate complex) with constant stirring is driven through the solution with dry nitrogen. It is stirred overnight at 60° C., after which 30 ml of methanol is instilled at 20° C. and hydrochloric acid is introduced with ice cooling. It is then briefly brought to a boil and suctioned off. The trihydrochloride is obtained in the form of colorless crystals (8.04 g; 86% of theory).

Melting point: 250° C. (decomposition)

| Analysis | | | | | |
|---|---|---|---|---|---|
| Cld: | C 41.45 | H 6.95 | N 13.18 | O 5.02 | Cl 33.37 |
| Fnd: | C 41.37 | H 6.89 | N 13.14 | | Cl 33.51 | f) 3,6,9-Triaza-4-(4-hydroxybenzyl)-3,6,9-tris-(tert-butoxycarbonylmethyl)-undecanedioic acid bis-(tert-butyl)diester 2.07 g (6.5 mmol) of the compound of example 1e and 5.2 g of sodium bicarbonate are put in 60 ml of dimethylformamide (dried over sodium hydride) and 6.34 g (82.2 mmol) of bromoacetic acid tert-butyl ester in 30 ml of dimethylformamide is instilled at 35° C. It is stirred for 2.5 hours more at 35° C., after which no initial product can be detected any longer by thin-film chromatography. It is filtered off from the precipitated sodium bromide and the filtrate is concentrated by evaporation. The residue is mixed with water and extracted several times with ether. After drying and concentration by evaporation the ether extract is purified of unreacted bromoacetic acid tert-butyl ester over a silica gel column. 3.54 g (68.8% of theory) of a colorless oil is obtained.

| Analysis | | | | |
|---|---|---|---|---|
| Cld: | C 63.13 | H 8.91 | N 5.38 | O 22.56 |
| Fnd: | C 63.21 | H 8.90 | N 5.42 | | g) 3,6,9-Triaza-4-(4-benzyloxycarbonylmethoxybenzyl)-3,6,9-tris-(tert-butoxycarbonylmethyl)-undecanedioic acid bis-(tert-butyl)-diester 1.98 g (2.54 mmol) of the compound according to example 1f is slowly combined with 70 mg of sodium hydride (80% in paraffin) (2.5 mmol) in 30 ml of dry tetrahydrofuran with stirring and then 0.54 g of bromoacetic acid benzyl ester (2.54 mmol) in 20 ml of dry tetrahydrofuran is instilled at room temperature. After stirring overnight, it is suctioned off from precipitated sodium bromide, concentrated by evaporation, taken up in diethyl ether and the remaining inorganic components are removed by washing with water. After drying on magnesium sulfate it is freed of the solvent and purified by a silica gel column. 1.35 g (1.45 mmol) of a colorless syrup (62% of theory) is obtained.

| Analysis | | | | |
|---|---|---|---|---|
| Cld: | C 64.70 | H 8.36 | N 4.52 | O 22.4 |
| Fnd: | C 64.91 | H 8.31 | N 4.55 | | h) 3,6,9-Triaza-3,6,9-tris-(tert-butoxycarbonylmethyl)-4-(4-carboxymethoxybenzyl)-undecanedioic acid bis-(tert-butyl)diester 7.83 g (8.43 mmol) of the compound according to example 1g is dissolved in 70 ml of dry tetrahydrofuran and hydrogenated in the presence of 1.4 g of 10% palladium carbon, until no further hydrogen absorption takes place. After suctioning, the solvent is removed on a rotation evaporator and the substance is dried at 0.01 torr. 4.2 g of a colorless oil (yield 74% of theory) is obtained.

| Analysis | | | | |
|---|---|---|---|---|
| Cld: | C 61.62 | H 8.53 | N 5.01 | O 24.81 |
| Fnd: | C 61.73 | H 8.53 | N 5.10 | | i) Poly-<4-[2,6-di-(bis-(carboxymethyl)-amino)-4-(carboxymethyl)-aza-hexyl]-phenoxyacetyl>-polyethylenimine 7.16 g (8.5 mmol) of the compound according to example 1h is mixed in 80 ml of tetrahydrofuran with 1.28 g (9.4 mmol) of chloroformic acid isobutyl ester and 1.9 g (18.8 mmol) of triethylamine, each dissolved in 20 ml tetrahydrofuran, at 0° C. with stirring.

After one hour, with the cooling being maintained, a solution of 533.2 mg (corresponds to 12.4 mmol of monomer subunit) of polyethylenimine (Polymin anhydrous$^{(R)}$) is added in water and allowed to come to room temperature with stirring. Precipitated salt is filtered off, the solvent is evaporated and the residue is dissolved by warming with 150 ml of formic acid. After 3 hours at 60° C., it is poured into 2 liters of ice water and dialyzed. After freeze-drying, 4.35 g of white, fine crystalline powder remains.

| Analysis: | | |
|---|---|---|
| C 51.75 | H 6.03 | N 10.54 | j) Gadolinium complex 2.36 g of the polymer complexing agent of example 1i is dissolved in 30 ml of water with addition of some drops of diluted ammonia solution and is mixed with 3.92 ml of a 1 m solution of gadolinium acetate in 0.1 m of ammonium acetate buffer of pH 4.5, and the pH is kept at a value above 5.5 by addition of diluted ammonia solution. It is dialyzed and subjected to a freeze-drying. 2.96 g of a white crystalline powder remains.

| Analysis: | | | |
|---|---|---|---|
| C 41.26 | H 4.41 | N 8.39 | Gd 20.67 |

Sodium salt of the gadolinium complex 1.8 g of the polymer complex is dissolved in 20 ml of water with stirring and addition of 1n of sodium hydroxide solution, and the pH must not exceed 7.5 (consumption 4.73 ml). After freeze-drying, the sodium salt is in the form of fine white crystals. The yield is 1.89 g.

| Analysis | | | | |
|---|---|---|---|---|
| C 39.0 | H 3.92 | N 7.94 | Na 5.71 | Gd 19.54 |

N-methylglucamine salt of the complex 2.16 g of the gadolinium complex is put in 50 ml of water and titrated with a 1 m aqueous solution of N-methylglucamine to a pH between 7.3 and 7.4. The consumption is 6.2 ml. After freeze-drying, 3.37 g of colorless crystals is present.

| Analysis: | | | |
|---|---|---|---|
| C 42.62 | H 4.21 | N 8.12 | Gd 13.9 |

EXAMPLE 2

Poly-<4-[2,6-di-(bis-carboxymethyl)-amino)-4-(carboxymethyl)-aza-hexyl]-phenoxyacetyl<-polyethylenimine-poly-[2-(maleimido)-ethylene amide]

3.81 g of the complexing agent obtained according to example 1 is dissolved in 8 ml of water with addition of 110 mg of potassium carbonate and quickly filled with 150 ml of dimethyl sulfoxide (DMSO). Then it is mixed with 200 mg of dimethyl sulfate in 1 ml of DMSO and warmed for 30 minutes to 60° C. Then 1.3 g (9.3 mmol) of 2-(maleimido)

-ethylamine is added, it is further warmed to 80° C. for 30 minutes and poured into the triple amount of water. After dialysis and freeze-drying, 4.0 g of white crystalline substance is present. A content of 78.9 mg (0.8 mmol) of maleimide/g substance is determined (=280 nm) by UV spectroscopy.

| Analysis: | | |
|---|---|---|
| C 51.75 | H 6.03 | N 10.56 |

The gadolinium complex and its salts are obtained as described in example 1j.

| Gadolinium complex | | | | |
|---|---|---|---|---|
| C 41.28 | H 4.41 | N 8.42 | Gd 20.63 | |
| Sodium salt | | | | |
| C 39.02 | H 3.92 | N 7.96 | Na 5.7 | Gd 19.40 |
| N-methylglucamine salt | | | | |
| C 42.63 | H 4.21 | N 8.14 | Gd 13.88 | |

Alternative method

If the reaction is performed according to the above formula, but the prepared Gd complex from example 1j is used instead of the complexing agent, the derivatized complex is also obtained after analogous working up. 7.78 g of the complex coated with amidoethylene-(maleimido) groups is obtained from 7.85 g of the gadolinium complex with 20.6% by weight of Gd. The product shows a gadolinium content of 20.1% by weight and 0.78 mg of maleimide per gram of substance.

EXAMPLE 3

Poly-<4-[2,6-di-(bis-(carboxymethyl)-amino)-4-(carboxymethyl)-aza-hexyl]-phenoxyacetyl>-polyethylenimine-polyhydrazide As described for example 2, the hydrazide of the complexing agent is obtained if, instead of 2-(maleimido)-ethylamine, an equivalent amount of hydrazine hydrate is added. The hydrazine content is colorimetrically determined (p-dimethylaminobenzaldehyde) at 22.8 mg (0.8 mmol) of hydrazine/g of substance. 3.87 g of hydrazide is obtained as white crystalline substance from 4.02 g of complexing agent.

| Analysis: | | |
|---|---|---|
| C 51.68 | H 6.07 | N 10.61 |

The gadolinium complex and its salts are obtained as described in example 1j.

| Gadolinium complex | | | | |
|---|---|---|---|---|
| C 41.21 | H 4.44 | N 8.46 | Gd 20.65 | |
| Sodium salt | | | | |
| C 38.96 | H 3.95 | N 8.00 | Na 5.70 | Gd 19.52 |
| N-methylglucamine salt | | | | |
| C 42.58 | H 4.23 | N 8.17 | Gd 13.89 | |

EXAMPLE 4

Poly-<4-[2,6-di-(bis-(carboxymethyl)-amino)-4-(carboxymethyl)-aza-hexyl]-phenoxyacetyl>-polyethylenimine-poly-[10-hydrazinocarbonyl)-decylamide]

If 11-amino-undecanoic acid-(tert-butoxycarbonyl)-hydrazide, instead of 2-(maleimido)-ethylamine is used, as nitrogen base in the process described in example 2, poly-<4-[2,6-di-(bis-(carboxymethyl)-amino)-4-(carboxymethyl)-aza-hexyl]-phenoxyacetyl>polyethylenimine-poly-[10-((tert-butoxycarbonyl)-hydrazinocarbonyl)decylamide] is obtained, from which the tert-butoxycarbonyl protecting groups are removed with formic acid, as described for example 1i. Thus 6.41 g of white solid substance is obtained from 6.30 g of complexing agent. The hydrazine content is determined colorimetrically at 18.7 mg (0.67 mmol) per gram of substance.

| Analysis: | | |
|---|---|---|
| C 51.81 | H 6.07 | N 10.67 |

The gadolinium complex and its salts are obtained as described in example 1j.

| Gadolinium complex | | | | |
|---|---|---|---|---|
| C 41.38 | H 4.45 | N 8.52 | Gd 20.52 | |
| Sodium salt | | | | |
| C 39.13 | H 3.96 | N 8.06 | Na 5.67 | Gd 19.40 |
| N-methylglucamine salt | | | | |
| C 42.69 | H 4.24 | N 8.21 | Gd 13.83 | |

EXAMPLE 5 a) 3,6,9-Triaza-3,6,9-tris-(tert-butoxycarbonylmethyl)-4-(4-oxiranylmethoxybenzyl)-undecanedioic acid bis-(tert-butyl)diester 16.35 g (21.0 mmol) of 3,6,9-triaza-4-(4-hydroxybenzyl)-3,6,9-tris-(tert-butoxycarbonylmethyl)-undecanedioic acid bis-(tert-butyl)diester (example 1f) is dissolved with 630 mg (21 mmol) of sodium hydride (80% in paraffin) in 300 ml of toluene with stirring and is mixed with a solution of 1.95 g (21 mmol) of epichlorohydrin in 20 ml of toluene at 40° C. After one hour it is carefully mixed with 100 ml of water. The phases are separated after shaking. Then the organic phase is concentrated by evaporation after drying. After chromatographic purification, 15.4 g (88% of theory) of colorless oil is present.

| Analysis | | | | |
|---|---|---|---|---|
| Cld: | C 63.20 | H 8.80 | N 5.02 | O 22.96 |
| Fnd: | C 63.35 | H 8.76 | N 5.09 | | b) Poly-<3-[4-[2,6-di-(bis-(carboxymethyl)-amino)-4-(carboxymethyl)-aza-hexyl]-phenoxy]-2-hydroxypropy>polyethylenimine 12.3 g (14.7 mmol) of 3,6,9-triaza-3,6,9-tris-(tert-butoxycarbonylmethyl)-4-(4-oxiranylmethoxybenzyl)- undecanedioic acid bis-(tert-butyl)diester is dissolved in 150 ml of methanol with 6.30 mg (14.65 mmol of monomer subunits) of polyethylenimine, and at first the temperature is kept at 5° C. It is allowed to warm to room temperature within an hour and then heated for one more hour to 60° C. After removal of the solvent, it is heated in 100 ml of formic acid for 3 hours to 60° C., poured into 2 liters of water and dialyzed. After freeze-drying, 6.22 g of a fine crystalline white powder is present, which begins to sinter above 150° C.

| Analysis: | | |
|---|---|---|
| C 52.17 | H 6.41 | N 9.42 |

The gadolinium complex and its salts are obtained as described in example 1j.

| Gadolinium complex | | | |
|---|---|---|---|
| C 41.51 | H 4.70 | N 7.50 | Gd 20.83 |
| Sodium salt | | | |
| C 39.22 | H 4.19 | N 7.08 | Na 5.75  Gd 19.69 |
| N-methylglucamine salt | | | |
| C 42.79 | H 4.40 | N 7.52 | Gd 13.97 |

EXAMPLE 6

Poly-<3-[4-[2,6-di-(bis-(carboxymethyl)-amino)-4-(carboxymethyl)-aza-hexyl]-phenoxy]-2-hydroxypropy>-polyethylenimine-poly-[2-(maleimido)-ethylene amide]

Analogously to the formula indicated in example 2, 2.9 g of the complexing agent obtained according to example 5 is reacted. 2.8 g of the title compound is obtained. Maleimide content (UV) 0.31% by weight.

| Analysis: | | |
|---|---|---|
| C 52.17 | H 6.41 | N 9.45 |

The gadolinium complex and its salts are obtained as described in example 1j.

| Gadolinium complex | | | |
|---|---|---|---|
| C 41.53 | H 4.70 | N 7.52 | Gd 20.79 |
| Sodium salt | | | |
| C 39.25 | H 4.19 | N 7.11 | Na 5.74  Gd 19.65 |
| N-methylglucamine salt | | | |
| C 42.80 | H 4.41 | N 7.59 | Gd 13.96 |

EXAMPLE 7

Poly-<3-[4-[2,6-di-(bis-(carboxymethyl)-amino)-4-(carboxymethyl)-aza-hexyl]-phenoxy]-2-hydroxypropyl>-polyethylenimine-polyhydrazide Analogously to the formula of example 3, 3.4 g of the hydrazide was obtained, starting from 3.5 g of the complexing agent obtained according to example 5. The hydrazine content is 14.0 mg per gram of substance.

| Analysis: | | |
|---|---|---|
| C 52.06 | H 6.47 | N 9.54 |

The gadolinium complex and its salts are obtained as described in example 1j.

| Gadolinium complex | | | |
|---|---|---|---|
| C 41.44 | H 4.75 | N 7.60 | Gd 20.80 |
| Sodium salt | | | |
| C 39.16 | H 4.24 | N 7.18 | Na 5.74  Gd 19.65 |
| N-methylglucamine salt | | | |
| C 42.74 | H 4.44 | N 7.58 | Gd 13.96 |

EXAMPLE 8

Poly-<3-[4-[2,6-di-(bis-(carboxymethyl)-amino)-4-(carboxymethyl)-aza-hexyl]-phenoxy]-2-hydroxypropyl>-polyethylenimine-poly-[10-(hydrazinocarbonyl)-decylamide]

Analogously to the formula indicated for example 4.5 g of the complexing agent obtained according to example 5 is reacted. 4.6 g of the title compound is obtained.

| Analysis: | | |
|---|---|---|
| C 52.22 | H 6.44 | N 9.54 |

The gadolinium complex and its salts are obtained as described in example 1j.

| Gadolinium complex | | | |
|---|---|---|---|
| C 41.61 | H 4.73 | N 7.60 | Gd 20.71 |
| Sodium salt | | | |
| C 39.33 | H 4.22 | N 7.18 | Na 5.72  Gd 19.57 |
| N-methylglucamine salt | | | |
| C 42.85 | H 4.43 | N 7.59 | Gd 13.92 |

EXAMPLE 9 a) 3-Aza-1-(4-hydroxybenzyl)-1,3,5-tri-tosyl-pentane-1,5-diamine 24.0 g (75.3 mmol) of 3-aza-1-(4-hydroxybenzyl)-pentane-1,5-diamine (as trihydrochloride, example 1e) is put into 250 ml of dry pyridine, and 37.9 g (198.7 mmol) of tosyl chloride, dissolved in 100 ml of pyridine, is instilled in an hour at 0° C. with good stirring. It is allowed to stand overnight at 4° C., the main part of the pyridine is evaporated in a vacuum and taken up in 300 ml of dichloromethane. The remaining pyridine and excess toluenesulfonic acid are removed by repeated washing with dilute hydrochloric acid, aqueous bicarbonate solution and bidistilled water. After drying, it is chromatographed on silica gel with ethyl acetate/hexane. The tritosylate is obtained in the form of colorless crystals. Yield 36.9 g (73% of theory).

Melting point: 145°–146° C.

| Analysis | | | | | |
|---|---|---|---|---|---|
| | C | H | N | O | S |
| Cld: | 57.20 | 5.55 | 6.25 | 16.66 | 14.31 |
| Fnd: | 57.15 | 5.32 | 6.24 | | 14.20 | b) 2-(4-hydroxybenzyl)-1,4,7,10-tetra-tosyl-1,4,7,10-tetraazacyclodecane 10.95 g (16.3 mmol) of 3-aza-1-(4-hydroxybenzyl)-1,3,5-tri-tosyl-pentane-1,5-diamine is dissolved in 100 ml of dimethylformamide and stirred with 1.35 g (45 mmol) of sodium hydride (80% in paraffin) for 30 minutes at 35°–40° C. Then it is slowly mixed with a solution of 9.51 g (16.3 mmol) of 3-aza-1,3,5-tri-tosyl-1,5-dihydroxypentane in 100 ml of DMF. It is stirred for four hours at 130° C., allowed to cool overnight and the solvent is distilled off. The residue crystallizes during trituration with a little methanol. After washing with dilute hydrochloric acid and recrystallizing from acetonitrile, 7.4 g (48% of theory) of colorless crystals with a melting point of 192°–193° C. is obtained.

| Analysis | | | | | |
|---|---|---|---|---|---|
| | C | H | N | O | S |
| Cld: | 53.84 | 5.25 | 5.84 | 21.68 | 13.37 |
| Fnd: | 53.66 | 5.17 | 5.81 | | 13.30 | c) 2-(4-hydroxybenzyl)-1,4,7,10-tetraazacyclododecane, trihydrobromide 12.0 g (12.7 mmol) of 2-(4-hydroxybenzyl)-1,4,7,10-tetra-tosyl-1,4,7,10-tetraazacyclodecane is heated in 50 ml of glacial acetic acid with 33% of hydrogen bromide for four hours to 100° C. It is poured into 300 ml of diethyl ether, suctioned off and resuspended twice in 300 ml of diethyl ether each. All operations are performed under nitrogen protective atmosphere. After drying in a vacuum, 5.16 g (78% of theory) is present of colorless crystals, which melt with decomposition at 115°–117° C.

| Analysis | | | | | |
|---|---|---|---|---|---|
| | C | H | N | O | Br |
| Cld: | 34.57 | 5.60 | 10.75 | 3.07 | 45.99 |
| Fnd: | 34.75 | 5.61 | 10.77 | | 45.64 | d) 2-(4-hydroxybenzyl)-1,4,5,10-tetrakis-(tert-butoxy-carbonylmethyl)-1,4,7,10-tetraazacyclododecane 8.49 g (16.3 mmol) of 2-(4-hydroxybenzyl)-1,4,7,10-tetraazacyclododecane (as trihydrobromide) is suspended in 150 ml of dimethylformamide, mixed with 9.66 g (115 mmol) of sodium bicarbonate and mixed at 60° C. with a solution of 12.7 g (65.2 mmol) of bromoacetic acid tert-butyl ester in 100 ml of DMF. After stirring for 2 hours at this temperature, the solvent is removed and the oily residue is chromatographed on silica gel with ether/hexane. A colorless viscous oil is obtained. Yield: 9.0 g (79%).

| Analysis | | | | |
|---|---|---|---|---|
| | C | H | N | O |
| Cld: | 63.73 | 9.05 | 7.62 | 19.59 |
| Fnd: | 63.70 | 8.97 | 7.50 | | e) 2-[4-(Oxiranylmethoxy)-benzyl]-1,4,7,10-tetrakis-(tert-butoxycarbonylmethyl)-1,4,7,10-tetraazacyclododecane 12.72 g (18.2 mmol) of 2-[4-hydroxybenzyl)-1,4,7,10-tetrakis-(tert-butoxycarbonylmethyl)-1,4,7,10-tetraazacyclododecane (example 9d) is dissolved in 250 ml of toluene and mixed with 350 mg of sodium hydride (80% in paraffin, 18.3 mmol). It is warmed to 80° to 100° C. and mixed by instillation with a solution of 1.74 g (18.2 mmol) of epichlorohydrin in 50 ml of toluene. After refluxing for two hours, it is concentrated by evaporation and purified over a silica gel column. A colorless oil is obtained.

Yield: 11.53 g (79.7% of theory)

| Analysis | | | | |
|---|---|---|---|---|
| | C | H | N | O |
| Cld: | 63.44 | 9.38 | 7.04 | 20.12 |
| Fnd: | 63.34 | 9.15 | 7.12 | | f) Poly-N-3-{4-[2,5,8,11-tetrakis-(carboxymethyl)-2,5,8,11-tetraazacyclododecylmethyl]-3-phenoxy}-2-hydroxypropyl-polyethylenimine.

As described for example 5, 7.49 g of white fine crystalline powder, which decomposes above 165° C., is obtained from 12 g (15.1 mmol) of 2-[4-(oxiranylmethoxy)-benzyl]-1,4,7,10-tetrakis-(tert-butoxycarbonylmethyl)-1,4,7,10-tetraazacyclododecane and 645 mg (15 mmol of monomer subunits) of polyethylenimine.

| Analysis: | | |
|---|---|---|
| C 55.16 | H 7.11 | N 11.52 |

The gadolinium complex and its salts are obtained as described in example 1j.

| Gadolinium complex | | | |
|---|---|---|---|
| C 44.03 | H 5.28 | N 9.18 | Gd 20.55 |
| | | Sodium salt | |
| C 42,80 | H 5.01 | N 8.93 | Na 2.92 Gd 19.98 |
| | | N-methylglucamine salt | |
| C 44.30 | H 4.99 | N 8.87 | Gd 15.55 |

EXAMPLE 10

Poly-N-3-{4-[2,5,8,11-tetrakis-(carboxymethyl)-2,5,8,11-tetraazacyclododecylmethyl]-3-phenoxy}-2-hydroxypropyl polyethylenimine-poly-[2-(maleimido)-ethylene amide]

Analogously to the formula for example 2, 3.9 g of the complexing agent obtained according to example 9 is reacted. 4.0 g of the title compound is obtained. Maleimide content (UV): 0.48% by weight.

| Analyis: | | |
|---|---|---|
| C 55.05 | H 7.16 | N 11.63 |

The gadolinium complex and its salts are obtained as described in example 1j.

| Gadolinium complex | | | | |
|---|---|---|---|---|
| C 43.96 | H 5.32 | N 9.29 | Gd 20.52 | |
| | | Sodium salt | | |
| C 42.74 | H 5.04 | N 9.03 | Na 2.91 | Gd 19.95 |
| | | N-methylglucamine salt | | |
| C 44.24 | H 5.03 | N 8.95 | Gd 16.53 | |

EXAMPLE 11

Poly-N-3-{4-[2,5,8,11-tetrakis-(carboxymethyl)-2,5,8,11-tetraazacyclododecylmethyl]-3-phenoxy}-2-hydroxypropyl-polyethylenimine-polyhydrazide Analogously to the formula for example 3, 2.5 g of the complexing agent obtained according to example 9 is reacted. 2.3 g of the title compound is obtained.

Hydrazinc content (colorim.): 0.35% by weight

| C 55.18 | H 7.14 | N 11.61 |
|---|---|---|

The gadolinium complex and its salts are obtained as described in example 1j.

| Gadolinium complex | | | | |
|---|---|---|---|---|
| C 42.89 | H 5.31 | N 9.28 | Gd 20.43 | |
| | | Sodium salt | | |
| C 42.89 | H 5.04 | N 9.03 | Na 2.9 | Gd 19.86 |
| | | N-methylglucamine salt | | |
| C 44.37 | H 5.02 | N 8.95 | Gd 16.47 | |

EXAMPLE 12

Poly-N-3-{4-[2,5,8,11-tetrakis-(carboxymethyl)-2,5,8,11-tetraazacyclododecylmethyl]-3-phenoxy}-2-hydroxypropyl-polyethylenimine-poly-[10-hydrazinocarbonyl)-decylamide]

Analogously to the formula indicated for example 4, 5.8 g of the complexing agent produced according to example 9 is reacted. 5.9 g of the title compound is obtained.

Hydrazine content (colorim.): 0.35% by weight

| Analysis: | | |
|---|---|---|
| C 55.14 | H 7.10 | N 11.55 |

The gadolinium complex and its salts are obtained as described in example 1j.

| Gadolinium complex | | | | |
|---|---|---|---|---|
| C 44.06 | H 5.28 | N 9.22 | Gd 20.48 | |
| | | Sodium salt | | |
| C 42.84 | H 5.01 | N 8.97 | Na 2.91 | Gd 19.91 |
| | | N-methylglucamine salt | | |
| C 44.32 | H 4.99 | N 8.91 | Gd 16.50 | |

EXAMPLE 13 a) $N^3$-(2,6-dioxomorpholinoethyl)-$N^6$-(ethoxycarbonylmethyl)-3,6-diazaoctanedioic acid A suspension of 21.1 g (50 mmol) of $N^3,N^6$-bis-(carbonylmethyl)-$N^9$-(ethoxycarboxymethyl)-3,6,9-triazaundecanedioic acid (J. Pharm. Sci. 68, 1979, 194) in 250 ml of acetic anhydride, after addition of 42.2 ml of pyridine, is allowed to stir for three days at room temperature. Then the precipitate is suctioned off, it is washed three times with 50 ml of acetic anhydride each and is then stirred for several hours with absolute diethyl ether. After suctioning off, washing with absolute diethyl ether and drying in a vacuum at 40° C., 18.0 g (=89% of theory) of a white powder with a melting point of 195°–196° C. is obtained.

Analysis (relative to anhydrous substance):

| | C | H | N |
|---|---|---|---|
| Cld: | 47.64 | 6.25 | 10.42 |
| Fnd: | 47.54 | 6.30 | 10.22 | b) Poly-N-[10-carboxy-3,6,9-tris(carboxymethyl)-3,6,9-triazadecanoyl]-polyethylenimine 380 mg of polyethylenimine (8.8 mmol monomer subunits) is dissolved in 50 ml of water. 2.37 g (5.9 mmol) of monoanhydride obtained according to 13a is added by portions with ice cooling, and the pH is kept above 9 with 1 n of sodium hydroxide solution. After stirring for one hour, it is dialyzed and freeze-dried.

Yield 1.48 g.

| Analysis: | | |
|---|---|---|
| C 46.55 | H 6.46 | N 14.51 | c) The gadolinium complex and its salts are obtained analogously to example 1j.

| Gadolinium complex | | | | |
|---|---|---|---|---|
| C 35.10 | H 4.41 | N 10.51 | Gd 26.22 | |
| | | Sodium salt | | |
| C 33.25 | H 4.02 | N 10.33 | N 3.72 | Gd 25.85 |
| | | N-methylglucamine salt | | |
| C 33.25 | H 4.02 | N 10.33 | Gd 20.40 | | d) The dysprosium complex and its salts are obtained as described in example 1j, if dysprosium acetate is used instead of gadolinium acetate.

| Dysprosium complex | | | | |
|---|---|---|---|---|
| C 34.24 | H 4.25 | N 10.66 | | Dy 26.94 |
| | | | Sodium salt | |
| C 33.04 | H 3.94 | N 10.28 | Na 3.67 | Dy 25.99 |
| | | N-methylglucamine salt | | |
| C 36.87 | H 4.15 | N 9.93 | | Dy 20.61 |

EXAMPLE 14

Poly-N-[10-carboxy-3,6,9-tris(carboxymethyl)-3,6,
9-triazadecanoyl]-polyethylenimine-poly-[2-
(maleimido)-ethylene amide]

Analogously to the formula indicated for example 2, 5.2 g of complexing agent obtained according to example 13 is reacted. 4.5 g of the title compound is obtained.

Maleimlde content (UV): 0.27% by weight

| Analysis: | | |
|---|---|---|
| C 46.53 | H 6.51 | N 14.51 |

The gadolinium complex and its salts are obtained as described in example 1j.

| Gadolinium complex | | | | |
|---|---|---|---|---|
| C 34.58 | H 4.28 | N 10.78 | | Gd 26.24 |
| | | | Sodium salt | |
| C 33.35 | H 3.95 | N 10.35 | Na 3.65 | Gd 25.30 |
| | | N-methylglucamine salt | | |
| C 37.12 | H 4.15 | N 10.00 | | Gd 20.05 |

EXAMPLE 15

Poly-N-[10-carboxy-3,6,9-tris(carboxymethyl)-3,6,
9-triazadecanoyl]-polyethylenimine-polyhydrazide Analogously to the formula indicated for example 3, 2.5 g of complexing agent obtained according to example 13 is reacted. 2.2 g of the title compound is obtained.

Hydrazine content (colorim.): 0.47% by weight

| Analysis: | | |
|---|---|---|
| C 64.47 | H 6.44 | N 14.49 |

The gadolinium complex and its salts are obtained as described in example 1j.

| Gadolinium complex | | | | |
|---|---|---|---|---|
| C 34.32 | H 4.26 | N 10.75 | | Gd 26.38 |
| | | | Sodium salt | |
| C 33.36 | H 3.96 | N 10.31 | Na 3.73 | Gd 25.39 |

| N-methylglucamine salt | | | |
|---|---|---|---|
| C 37.04 | H 4.15 | N 9.95 | Gd 20.19 |

EXAMPLE 16

Poly-N-[10-carboxy-3,6,9-tris(carboxymethyl)-3,6,
9-triazadecanoyl]-polyethylenimine-poly-[10-
(hydrazinocarbonyl)decylamide]

Analogously to the formula indicated for example 4, 2.8 g of the complexing agent produced according to example 13 is reacted. 2.9 g of the title compound is obtained.

Hydrazine content (colorim.): 0.31% by weight

| Analysis: | | |
|---|---|---|
| C 46.66 | H 6.43 | N 14.55 |

The gadolinium complex and its salts are obtained as described in example 1j.

| Gadolinium complex | | | | |
|---|---|---|---|---|
| C 34.44 | H 4.27 | N 10.72 | | Gd 26.20 |
| | | | Sodium salt | |
| C 33.39 | H 3.96 | N 10.35 | Na 3.72 | Gd 25.48 |
| | | N-methylglucamine salt | | |
| C 37.07 | H 4.19 | N 9.96 | | Gd 20.00 |

EXAMPLE 17 a) 3-Aza-2-(4-benzyloxybenzyl)-4-oxoglutaric diamide (Method A)

3.62 g (13.3 mmol) of O-benzyltyrosine amide is refluxed with 2.7 g of ethyloxamate (23 mmol) for 14 hours in dimethoxyethane. After removal of the solvent, it is successively washed with water, ethanol and ether. After drying, 2.73 g of white crystals (60% of theory) is obtained.

Melting point: 270° C.

| | Analysis | | | |
|---|---|---|---|---|
| | C | H | N | O |
| Cld: | 63.33 | 5.61 | 12.30 | 18.74 |
| Fnd: | 63.24 | 5.52 | 12.14 | | or according to method B.

α) 3-Aza-2-(4-benzyloxybenzyl)-4-oxoglutaric acid-
5-ethyl ester-1-amide 3 g (11.1 mmol) of O-benzyltryrosinamide is dissolved in 30 ml of dimethoxyethane, mixed with 1.56 ml of triethylamine and 1.53 g (11.1 mmol) of oxalic acid ethyl ester chloride is instilled at 0° C. After 30 minutes at 0° C., it is poured on 100 ml of ice, suctioned off and dried. The yield is 3.67 g (94% of theory).

Melting point: 142° C.

| | Analysis | | | |
|---|---|---|---|---|
| | C | H | N | O |
| Cld: | 64.85 | 5.98 | 7.56 | 21.59 |
| Fnd: | 64.71 | 6.11 | 7.46 | |

β) 3.6 g (9.72 mmol) of the compound according to example a is covered with 40 ml of a solution of 1 mol of $NH_3$/l methanol. After one hour, the precipitated product is filtered off. After drying, 3.13 g (95% of theory) of the title compound is obtained in the form of colorless crystals.

Melting point: 269° C.

| | Analysis | | | |
|---|---|---|---|---|
| | C | H | N | O |
| Cld: | 63.33 | 5.61 | 12.30 | 18.74 |
| Fnd: | 63.25 | 5.63 | 12.17 | | b) 3-Aza-2-(4-hydroxybenzyl)-4-oxoglutaric acid diamide 1 g (2.9 mmol) of the compound of example 17a is suspended with 100 mg of 10% palladium carbon and a few drops of concentrated hydrochloric acid in 20 ml of methanol ana hydrogenated to the end of the hydrogen absorption. After filtering off of the catalyst, 690 mg of colorless crystals (93% of theory) is obtained.

Melting point: 245°–250° C. (decomposition)

| | Analysis | | | |
|---|---|---|---|---|
| | C | H | N | O |
| Cld: | 52.58 | 5.21 | 16.72 | 25.47 |
| Fnd: | 52.83 | 5.19 | 16.84 | | c) 3-Aza-2-(4-hydroxybenzyl)-pentane-1,5-diaminetrihydrochloride 1 g of the compound according to example b is reacted according to the formula indicated for example 1e. The colorless crystallizate obtained weighs 1.19 g (93.7% of theory).

Melting point: 238° C.

| | Analysis | | | | |
|---|---|---|---|---|---|
| | C | H | N | O | Cl |
| Cld: | 41.61 | 6.98 | 13.23 | 5.03 | 33.13 |
| Fnd: | 41.60 | 6.95 | 13.17 | | 33.33 | d) 3,6,9-Triaza-3,6,9-tris-(tert-butoxycarbonylmethyl)-5-(4-hydroxybenzyl)-undecanedioic acid-bis-(tert-butyl)diester According to the formula indicated for example 1f, 5.19 g (16.3 mmol) of the title compound of example c is reacted to 7.75 g (61% of theory) of the title compound in the form of a viscous clear liquid.

| | Analysis | | | |
|---|---|---|---|---|
| | C | H | N | O |
| Cld: | 63.13 | 8.91 | 5.38 | 22.56 |
| Fnd: | 63.00 | 8.92 | 5.29 | | e) 3,6,9-Triaza-5-(4-benzyloxycarbonylmethoxybenzyl)-3,6,9-tris-(tert-butoxycarbonylmethyl)-undecanedioic acid bis-(tert-butyl)diester 5.0 g (6.4 mmol) of title compound of example d is reacted according to the formula for example 1g with bromoacetic acid benzyl ester to 4.6 g (74.8% of theory) of a colorless, viscous oil.

| | Analysis | | | |
|---|---|---|---|---|
| | C | H | N | O |
| Cld: | 64.70 | 8.26 | 4.52 | 22.40 |
| Fnd: | 64.46 | 8.30 | 4.49 | | f) 3,6,9-Triaza-3,6,9-tris-(tert-butoxycarbonylmethyl)-5-(4-carboxymethoxybenzyl)-undecanedioic acid bis-(tert-butyl)diester 4.1 g of a colorless viscous oil (93.2% of theory) is obtained according to the formula indicated under example 1h from 4.9 g (5.16 mmol) of the benzyl ester obtained in the previous reaction step.

| | Analysis | | | |
|---|---|---|---|---|
| | C | H | N | O |
| Cld: | 61.62 | 8.53 | 5.01 | 24.81 |
| Fnd: | 61.66 | 8.45 | 5.15 | | g) Poly-[4-[5-(bis-carboxymethyl)-amino]-3-(carboxymethyl)-aza-2-[bis-(carboxymethyl)-aminomethyl]-pentyl]phenoxyacetyl]-polyethylenimine The title compound is synthesized according to the formula for example 1i from 3.27 g of the pentaester described in the previous reaction step and 245 mg of polyethylenimine. Thus, 2.0 g of the polymer complexing agent is obtained as white crystalline powder.

| Analysis: | | |
|---|---|---|
| C 51.76 | H 6.04 | N 10.56 |

The gadolinium complex and its salts are obtained as described in example 1j.

| | | Gadolinium complex | | |
|---|---|---|---|---|
| C 41.32 | H 4.42 | N 8.45 | | Gd 20.70 |
| | | Sodium salt | | |
| C 38.91 | H 3.91 | N 7.94 | Na 5.71 | Gd 19.58 |
| | | N-methylglucamine salt | | |
| C 42.60 | H 4.23 | N 8.13 | | Gd 13.87 |

EXAMPLE 18

Poly-[4-<5-{bis-(carboxymethyl)-amino}3-(carboxymethyl)-aza-2-[2-(bis-(carboxymethyl)-amino-methyl]-pentyl>-phenoxyacetyl] polyethylenimine-poly-[2-(maleimido)-ethylene amide]

Analogously to the formula indicated for example 2, 4.3 g of the complexing agent obtained according to example 17 is reacted. 4.1 g of the title compound is obtained. Maleimide content (UV) 0.68% by weight.

| | Analysis: | |
|---|---|---|
| C 51.74 | H 6.05 | N 10.55 |

The gadolinium complex and its salts are obtained as described in example 1j.

| | | Gadolinium complex | | |
|---|---|---|---|---|
| C 41.09 | H 4.43 | N 8.43 | | Gd 20.69 |
| | | Sodium salt | | |
| C 38.95 | H 3.93 | N 7.98 | Na 5.71 | Gd 19.50 |
| | | N-methylglucamine salt | | |
| C 42.54 | H 4.21 | N 8.15 | | Gd 13.88 |

EXAMPLE 19

Poly-[4-<5-{bis-(carboxymethyl)-amino}3-(carboxymethyl)-aza-2-[2-(bis-(carboxymethyl)-amino)-methyl]-pentyl>-phenoxyacetyl]-polyethylenimine-polyhydrazide Analogously to the formula indicated for example 3, 2.6 g of the complexing agent obtained according to example 17 is reacted. 2.5 g of the title compound is obtained.

Hydrazine content (colorim.) 0.32% by weight

| | Analysis: | |
|---|---|---|
| C 51.91 | H 6.05 | N 10.52 |

The gadolinium complex and its salts are obtained as described in example 1j.

| | | Gadolinium complex | |
|---|---|---|---|
| C 41.06 | H 4.41 | N 8.43 | Gd 20.71 |

| | | Sodium salt | | |
|---|---|---|---|---|
| C 39.13 | H 3.93 | N 7.93 | Na 5.73 | Gd 19.48 |
| | | N-methylglucamine salt | | |
| C 42.57 | H 4.21 | N 8.11 | | Gd 13.92 |

EXAMPLE 20

Poly-[4-<5{bis-(carboxymethyl)-amino}-3-(carboxymethyl)-aza-2-[2-(bis-(carboxymethyl)-amino)-methyl]-pentyl>-phenoxyacetyl]-polyethylenimine-poly-[10-(hydrazinocarbonyl)-decylamide]

Analogously to the formula indicated for example 4, 2.8 g of the complexing agent obtained according to example 17 is reacted. 2.9 g of the title compound is obtained.

Hydrazine content (colorim.) 0.77% by weight

| | Analysis: | |
|---|---|---|
| C 52.03 | H 6.09 | N 10.65 |

The gadolinium complex and its salts are obtained as described in example 1j.

| | | Gadolinium complex | | |
|---|---|---|---|---|
| C 41.29 | H 4.47 | N 8.52 | | Gd 20.52 |
| | | Sodium salt | | |
| C 39.14 | H 3.96 | N 8.06 | Na 5.67 | Gd 19.40 |
| | | N-methylglucamine salt | | |
| C 42.76 | H 4.24 | N 8.17 | | Gd 13.79 |

EXAMPLE 21 a) 3,6-Diaza-3,6-bis-(tert-butoxycarbonylmethyl)-4-(4-hydroxybenzyl)-suberic acid bis-(tert-butyl) diester 15.31 g (0.064 mol) of 4-hydroxybenzyl-1,2-ethane diamine as dihydrochloride and 71.14 g (0.71 mol) of potassium bicarbonate were put in 380 ml of dimethylformamide (dried over sodium hydride) and 50 g (0.26 mol) of bromoacetic acid tert-butyl ester in 80 ml of dimethylformamide is instilled at 35° C. It is stirred for 2.5 hours more at 35° C., after which no initial product is any longer detected by thin-film chromatography. It is filtered off from the precipitated potassium bromide and the filtrate is concentrated by evaporation. The residue is mixed with water and extracted with ether several times. After drying and concentration by evaporation, the ether extract is purified from unreacted bromoacetic acid tert-butyl ester on a silica gel column. 24.8 g (63% of theory) of a colorless oil is obtained.

|      | Analysis |      |      |       |
|------|----------|------|------|-------|
|      | C        | H    | N    | O     |
| Cld: | 63.64    | 8.73 | 4.49 | 23.12 |
| Fnd: | 63.78    | 8.69 | 4.41 |       | b) Poly-[4-(2,3-di-(bis-(carboxymethyl))-aminopropyl>phenyliminocarbamate]-polyethylenimine 7.2 g (11.56 mmol) of the title compound of a) is dissolved in 150 ml of methanol and mixed by portions with 1.4 g (13.3 mmol) of cyanogen bromide, and at the same time an equimolar amount of 0.1 n methanolic potassium hydroxide is instilled. In this case the temperature must not exceed 10° C. After 15 minutes it is mixed with a solution of 470 mg (10.9 mmol of monomer subunits) of polyethylenimine in 20 ml of methanol and slowly heated to 40° C. After a half hour at this temperature, the solvent is evaporated (after previously filtering off a possible precipitate) and the residue is dissolved in 150 ml of formic acid with warming. After 2 hours at 60° C., it is poured into 2 liters of ice water, dialyzed and the retentate is subjected to a freeze-drying. The white flocculent crystallizate begins to decompose above 80° C. The yield is 3.56 g.

| Analysis: |       |       |
|-----------|-------|-------|
| C 51.52   | H 5.65 | N 12.13 |

The gadolinium complex and its salts are obtained as described in example 1j.

| Gadolinium complex | | | |
|---|---|---|---|
| C 38.59 | H 3.77 | N 9.14 Sodium salt | Gd 25.10 |
| C 37.45 | H 3.47 | N 8.80   Na 3.57 N-methylglucamine salt | Gd 24.37 |
| C 40.14 | H 3.78 | N 8.76 | Gd 19.46 |

EXAMPLE 22

Poly-[4-<2,3-di-(bis-(carboxymethyl))-aminopropyl>-phenyliminocarbamate]-polyethylenimine-poly-[2-(maleimido)ethylamide]

Analogously to the formula indicated for example 2, 2.5 g of the complexing agent obtained according to example 21 is reacted. 2.2 g of the title compound is obtained.

Maleimide content (UV) 0.67% by weight

| Analysis: | C 51.46 | H 5.66 | N 12.18 |
|---|---|---|---|

The gadolinium complex and its salts are obtained as described in example 1j.

| Gadolinium complex | | | |
|---|---|---|---|
| C 38.85 | H 3.77 | N 9.10 Sodium salt | Gd 25.17 |
| C 37.63 | H 3.48 | N 8.80   Na 3.55 N-methylglucamine salt | Gd 24.42 |
| C 40.36 | H 3.79 | N 8.80 | Gd 19.50 |

EXAMPLE 23

Poly-[4<2,3-di-(bis-(carboxymethyl))-aminopropyl>-phenyliminocarbamate]-polyethylenimine-polyhydrazide Analogously to the formula indicated for example 3, 4.4 g of the complexing agent obtained according to example 21 is reacted. 4.2 g of the title compound is obtained.

Hydrazine content (colorim.) 0.32% by weight

| Analysis: | C 51.64 | H 5.66 | N 12.08 |
|---|---|---|---|

The gadolinium complex and its salts are obtained as described in example 1j.

| Gadolinium complex | | | |
|---|---|---|---|
| C 38.79 | H 3.77 | N 9.09 Sodium salt | Gd 25.21 |
| C 37.57 | H 3.48 | N 8.77   Na 3.54 N-meglumine salt | Gd 24.44 |
| C 40.41 | H 3.79 | N 8.80 | Gd 19.48 |

EXAMPLE 24

Poly-[4-<2,3-di-(bis-(carboxymethyl))-aminopropyl>-phenyliminocarbamate]-polyethylenimine-poly-[10-(hydrazinocarbonyl)-decylamide]

Analogously to the formula indicated for example 4, 3.1 g of the complexing agent obtained according to example 21 is reacted. 3.2 g of the title compound is obtained.

Hydrazine content (colorim.) 0.17% by weight

| Analysis: | C 51.43 | H 5.70 | N 12.16 |
|---|---|---|---|

The gadolinium complex and its salts are obtained as described in example 1j.

| Gadolinium complex | | | |
|---|---|---|---|
| C 39.03 | H 3.81 | N 9.24 Sodium salt | Gd 25.02 |
| C 37.41 | H 3.51 | N 8.93   Na 3.53 N-meglumine salt | Gd 24.35 |
| C 40.56 | H 3.82 | N 8.81 | Gd 19.40 |

EXAMPLE 25 a) N-carbobenzoxyserine-(2-carbobenzoxyaminoethylene)-amide 7.34 g (30.7 mmol) of N-carbobenzoxyserine is dissolved in 120 ml of dry tetrahydrofuran, mixed with 5 ml of $Et_3N$ and then 2.9 ml of chloroformic acid ethyl ester is instilled, and the temperature is kept under $-10°$ C. After completion of the addition, it is stirred for 30 minutes at this temperature, again mixed with the same amount of pre-cooled triethylamine and an ice-cold solution of 7.1 g (30.7 mmol) of N-(2-aminoethyl)-carbamic acid benzyl ester hydrochloride in 70 ml of dimethylformamide is instilled. It is stirred for 30 more minutes at $-10°$ C., then allowed to come to room temperature with stirring, and then is heated for 10 minutes to $30°$ C. Then the solvent is removed on a rotation evaporator and pouring on 500 ml of ice water is performed. The crystallizate is suctioned off, washed with ice water and dried. The yield is 10.33 g (81% of theory).

Melting point: 167° C.

| Analysis | Cld: | C 60.71 | H 6.06 | N 10.11 | O 23.10 |
|---|---|---|---|---|---|
| | Fnd: | C 60.75 | H 5.98 | N 10.15 | | b) (2-Aminoethyl)serinamide 13.46 g (32.4 mmol) N-carbobenzoxyserine-(2-carbobenzoxyaminoethylene)-amide is hydrogenated in 200 ml of methanol in the presence of 1.37 g 10% palladium/carbon until no more hydrogen is absorbed. The catalyst is filtered off and leaving portions are removed on the oil pump. A viscous partly crystalline oil remains.

Yield 4.67 (98% of theory)

| Analysis | Cld: | C 40.80 | H 8.89 | N 28.55 | O 21.74 |
|---|---|---|---|---|---|
| | Fnd: | C 40.71 | H 8.85 | N 28.30 | | c) 1-hydroxymethyl-1,3,5-triazapentane, trihydrochloride 4.3 g (29.3 mmol) of (2-aminoethyl)-serinamide (example 25b) is suspended in 130 ml of dry tetrahydrofuran and a slow current of $B_2H_6$ (from 5.6 g of $NaBH_4$ in 75 ml of diethyleneglycoldimethyl ether and 54 ml of boron trifluoride etherate complex) with dry nitrogen, with constant stirring, is driven through the solution. It is stirred overnight at 60° C., then 30 ml of methanol is instilled at 20° C. and hydrochloric acid is introduced with ice cooling. Then it is briefly brought to a boil and suctioned off. The trihydrochloride is obtained as white, crystalline powder in 69% yield.

Melting point: 236° C. (decomposition)

| Analysis | Cld: | C 24.75 | H 7.47 | N 17.32 | O 6.59 | Cl 43.84 |
|---|---|---|---|---|---|---|
| | Fnd: | C 24.71 | H 7.40 | N 17.41 | | Cl 43.75 | d) 3,6,9-triaza-3,6,9-tris-(tert-butoxycarbonylmethyl)-4-hydroxymethyl-undecanedioic acid bis-(tert-butyl)diester 17.85 g (73.59 mmol) of the triamine obtained according to 25c) is put in 450 ml of dimethylformamide and mixed with 54.4 g (648 mmol) of sodium bicarbonate. 78.95 g (404.72 mmol) of bromoacetic acid tert-butyl ester is instilled at 35° C. with stirring, then it is stirred for 3 more hours at 35° C. and filtered from the precipitated salt. After concentration by evaporation, the residue is mixed with water and extracted several times with ether. The unreacted bromoacetic acid ester is separated on a silica gel column and, after removal of the solvent, 42.32 g (60.12 mmol) of a colorless viscous oil is obtained. (81.7% of theory)

| Analysis | Cld: | C 59.72 | H 9.30 | N 5.97 | O 25.0 |
|---|---|---|---|---|---|
| | Fnd: | C 59.66 | H 9.17 | N 5.92 | | e) 3,6,9-Triaza-3,6,9-tris-(tert-butoxycarbonylmethyl)-4-[(oxiranylmethoxy)-methyl]-undecanedioic acid bis-(tert-butyl)diester 24.16 g (34.32 mmol) of the hydroxymethyl compound obtained according to 25d) is dissolved with 1.47 g (37.76 mmol) of sodium amide in 500 ml of dry toluene and is slowly mixed at 40° C. with a solution of 3.46 g (37.41 mmol) of epichlorohydrin in 50 ml of toluene. After one hour of stirring at this temperature the insoluble is suctioned off, concentration by evaporation and purification on a silica gel column are performed. 24.0 g (31.58 mmol) of colorless oil remains. (92% of theory)

| Analysis | Cld: | C 60.05 | H 9.15 | N 5.53 | O 25.26 |
|---|---|---|---|---|---|
| | Fnd: | C 60.11 | H 9.32 | N 5.49 | | f) Poly-<6,10-di-[bis-(carboxymethyl)-amino]-8-[(carboxymethyl)-aza]-2-hydroxy-4-oxa-decyl>-polyethylenimine As described for example 5, the title compound is obtained from 4.2 g of the compound obtained in the previous reaction step and 230 mg of polyethylenimine as colorless crystalline powder in a yield of 2.31 g. Above 145° C. the compound sinters with gradual darkening.

| Analysis: | C 45.99 | H 6.57 | N 10.77 |
|---|---|---|---|

The gadolinium complex and its salts are obtained as described in example 1j.

| Gadolinium complex | | | |
|---|---|---|---|
| C 35.51 | H 4.63 | N 8.32 | Gd 23.18 |
| | | Sodium salt | |
| C 33.28 | H 4.06 | N 7.08  Na 6.34 | Gd 21.67 |
| | | N-meglumine salt | |
| C 39.08 | H 4.32 | N 8.08 | Gd 15.05 |

EXAMPLE 26

Poly-<6,10-di-[bis-(carboxymethyl)-amino]-8-[(carboxymethyl)-aza]-2-hydroxy-4-oxa-decyl>-polyethylenimine-[2-(maleimido)-ethyleneamide]

Analogously to the formula indicated for example 2, 2.5 g of the complexing agent obtained according to example 25 is reacted. 2.4 g of the title compound is obtained.

Maleimide content (UV) 0.30% by weight

| Analysis: | C 46.17 | H 6.54 | N 10.8 |
|---|---|---|---|

The gadolinium complex and its salts are obtained as described in example 1j.

| Gadolinium complex | | | |
|---|---|---|---|
| C 35.43 | H 4.65 | N 8.41<br>Sodium salt | Gd 23.20 |
| C 33.45 | H 4.09 | N 7.83    Na 6.31<br>N-meglumine salt | Gd 21.77 |
| C 39.23 | H 4.35 | N 8.10 | Gd 14.90 |

EXAMPLE 27

Poly-<6,10-di-[bis-(carboxymethyl)-amino]-8-[(carboxymethyl)-aza]-2-hydroxy-4-oxa-decyl>-polyethylenimine-polyhydrazide Analogously to the formula indicated for example 3, 2.3 g of the complexing agent obtained according to example 25 is reacted. 2.3 g of the title compound is obtained.

Hydrazine content (colorim.) 0.37% by weight

| Analysis: | C 45.89 | H 6.59 | N 10.75 |
|---|---|---|---|

The gadolinium complex and its salts are obtained as described in example 1j.

| Gadolinium complex | | | |
|---|---|---|---|
| C 35.66 | H 4.64 | N 8.29<br>Sodium salt | Gd 23.11 |
| C 33.42 | H 4.05 | N 7.82    Na 6.35<br>N-meglumine salt | Gd 21.7 |
| C 39.12 | H 4.32 | N 8.01 | Gd 15.00 |

EXAMPLE 28

Poly-<6,10-di-[bis-(carboxymethyl)-amino]-8-[(carboxymethyl)-aza-]-2-hydroxy-4-oxa-decyl>-polyethylenimine-poly-[10-(hydrazinocarbonyl)-decylamide]

Analogously to the formula indicated for example 4, 3.0 g of the complexing agent obtained according to example 25 is reacted. 3.1 g of the title compound is obtained.

Hydrazine content (colorim.) 0.46% by weight

| Analysis: | C 46.06 | H 6.61 | N 10.81 |
|---|---|---|---|

The gadolinium complex and its salts are obtained as described in example 1j.

| Gadolinium complex | | | |
|---|---|---|---|
| C 35.74 | H 4.66 | N 8.39<br>Sodium salt | Gd 23.05 |
| C 33.32 | H 4.08 | N 7.90    Na 6.33<br>N-meglumine salt | Gd 21.6 |
| C 39.25 | H 4.33 | N 8.06 | Gd 14.99 |

EXAMPLE 29

Poly-[4-<2,6-di-(bis-(carboxymethyl)-amino)-4-(carboxymethyl)-aza-hexyl>-phenoxyacetyl]-polylysine Into a solution of 3.21 g (25 mmol of lysyl subunits) of polylysine and 2.8 g of KOH in 150 ml of water is instilled, at 0° C., a solution, which has been produced from 25.14 g (30 mmol) of the title compound of example 1h, 4.7 g (30 mmol) of chloroformic acid isobutyl ester and 3.03 g (30 mmol) of triethylamine in 100 ml of tetrahydrofuran at 0° C. After the addition is completed, it is decanted from the precipitate and the latter is washed with water. The precipitate is dissolved in 250 ml of warm formic acid and then heated for 2 hours at 50° C. Then it is poured into 3 liters of water, dialyzed and the retentate is subjected to a freeze-drying. Fine white crystals are obtained in a yield of 9.07 g.

| Analysis: | C 52.25 | H 6.15 | N 10.63 |
|---|---|---|---|

The gadolinium complex and its salts are obtained as described in example 1j.

| Gadolinium complex | | | |
|---|---|---|---|
| C 42.51 | H 4.65 | N 8.68<br>Sodium salt | Gd 19.04 |
| C 40.55 | H 4.20 | N 8.20    Na 5.28<br>N-meglumine salt | Gd 18.07 |
| C 43.63 | H 4.40 | N 8.34 | Gd 13.16 |

EXAMPLE 30

Poly-[4-<2,6-di-(bis-(carboxymethyl)-amino)-4-(carboxymethyl)-aza-hexyl>-phenoxyacetyl]-polylysine-poly-[2-(maleimido)-ethylene amide]

Analogously to the formula indicated for example 2, 4.3 g of the complexing agent obtained according to example 29 is reacted. 4.1 g of the title compound is obtained.

Maleimide content (UV) 0.35% by weight

| Analysis: | C 52.41 | H 6.16 | N 10.64 |
|---|---|---|---|

The gadolinium complex and its salts are obtained as described in example 1j.

| | | Gadolinium complex | | |
|---|---|---|---|---|
| C 44.42 | H 4.66 | N 8.68 Sodium salt | | Gd 18.84 |
| C 40.60 | H 4.17 | N 8.28 N-meglumine salt | Na 5.25 | Gd 17.95 |
| C 43.23 | H 4.38 | N 8.33 | | Gd 13.01 |

EXAMPLE 31

Poly-<4-[2,6-di-(bis-(carboxymethyl)-amino)-4-(carboxymethyl)-aza-hexyl]-phenoxyacetyl>-polylysine-poly-hydrazide Analogously to the formula indicated for example 3, 4.6 g of the complexing agent obtained according to example 29 is reacted. 4.5 g of the title compound is obtained.

Hydrazine content (colorim.) 0.52% by weight

| Analysis: | C 52.29 | H 6.13 | N 10.63 |
|---|---|---|---|

The gadolinium complex and its salts are obtained as described in example 1j.

| | | Gadolinium complex | | |
|---|---|---|---|---|
| C 42.47 | H 4.64 | N 8.67 Sodium salt | | Gd 19.03 |
| C 40.34 | H 4.20 | N 8.21 N-meglumine salt | Na 5.25 | Gd 17.93 |
| C 43.59 | H 4.37 | N 8.32 | | Gd 13.14 |

EXAMPLE 32

Poly-<4-[2,6-di-(bis-(carboxymethyl)-amino)-4-(carboxymethyl)-aza-hexyl]-phenoxyacetyl>-polylysine-[10-(hydrazinocarboxyl)-decylamide]

Analogously to the formula indicated for example 4, 5.3 g of the complexing agent obtained according to example 29 is reacted. 5.4 g of the title compound is obtained.

Hydrazine content (colorim.) 0.31% by weight

| Analysis: | C 52.3 | H 6.17 | N 10.69 |
|---|---|---|---|

The gadolinium complex and its salts are obtained as described in example 1j.

| | | Gadolinium complex | | |
|---|---|---|---|---|
| C 42.77 | H 4.65 | N 8.70 Sodium salt | | Gd 18.84 |
| C 40.41 | H 4.18 | N 8.29 N-meglumine salt | Na 5.24 | Gd 17.87 |
| C 43.34 | H 4.40 | N 8.33 | | Gd 13.09 |

EXAMPLE 33

Poly-[3->4-[2,6-di-(bis-(carboxymethyl)-amino)-4-(carboxymethyl)-aza-hexyl]-phenoxy>-2-hydroxypropyl]-polylysine To a solution of 1.76 g (13.75 mmol of lysyl subunits) of polylysine in 100 ml of water with 1.39 g of triethylamine is added, at 0° C., a solution of 8.1 g (14.58 mmol) of 3,6,9-triaza-3,6,9-tris-(carboxymethyl)-4-[4-(oxiranylmethoxy)-benzyl]-undecanedioic acid (produced from the corresponding penta(tert-butyl ester) of example 5a by warming of formic acid according to the formula of example 1i) in 150 ml of 0.1 n sodium hydroxide solution. It is allowed to warm to room temperature, dialyzed and the retentate is subjected to a freeze-drying. 8.36 g of fine needle-shaped substance is obtained.

| Analysis: | C 55.27 | H 7.14 | N 11.62 |
|---|---|---|---|

The gadolinium complex and its salts are obtained as described in example 1j.

| | | Gadolinium complex | | |
|---|---|---|---|---|
| C 45.01 | H 5.43 | N 9.41 Sodium salt | | Gd 19.26 |
| C 43.80 | H 5.17 | N 9.18 N-meglumine salt | Na 2.74 | Gd 18.81 |
| C 44.79 | H 5.14 | N 4.05 | | Gd 15.75 |

EXAMPLE 34

Poly-[3-<4-[2,6-di-(bis-(carboxymethyl)-amino)-4-(carboxymethyl)-aza-hexyl]-phenoxy>-2-hydroxypropyl]-polylysinepoly-[2-(maleimido)-ethylene amide]

Analogously to the formula indicated for example 2, 5.3 g of the complexing agent obtained according to example 33 is reacted. 5.1 g of the title compound is obtained.

Maleimide content (UV) 0.44% by weight

| Analysis: | C 55.43 | H 7.11 | N 25.90 |
|---|---|---|---|

The gadolinium complex and its salts are obtained as described in example 1j.

| | | Gadolinium complex | | |
|---|---|---|---|---|
| C 45.02 | H 5.43 | N 9.43 Sodium salt | | Gd 19.14 |
| C 43.85 | H 5.14 | N 9.16 N-meglumine salt | Na 2.74 | Gd 18.73 |
| C 44.92 | H 5.13 | N 9.08 | | Gd 15.65 |

EXAMPLE 35

Poly-{3-<4-[2,6-di-(bis-(carboxymethyl)-amino )-4-(carboxymethyl)-aza-hexyl]-phenoxy>2-hydroxypropyl}-polylysinepoly-hydrazide Analogously to the formula indicated for example 3, 4.7 g of the complexing agent obtained according to example 33 is reacted. 4.6 g of the title compound is obtained.

Hydrazine content (colorim.) 0.12% by weight

| Analysis: | C 55.19 | H 7.12 | N 11.59 |
|---|---|---|---|

The gadolinium complex and its salts are obtained as described in example 1j.

| Gadolinium complex | | | |
|---|---|---|---|
| C 44.77 | H 5.40 | N 9.43 | Gd 19.17 |
| | | Sodium salt | |
| C 43.83 | H 5.14 | N 9.20  Na 2.75 | Gd 18.67 |
| | | N-meglumine salt | |
| C 45.08 | H 5.11 | N 9.10 | Gd 15.66 |

EXAMPLE 36

Poly-{3-<4-[2,6-di-(bis-(carboxymethyl)-amino)-4-(carboxymethyl)-aza-hexyl]-phenoxy>2-hydroxypropyl}-polylysine-poly-[10-(hydrazinocarbonyl)-decylamide]

Analogously to the formula indicated for example 4, 3.8 g of the complexing agent obtained according to example 33 is reacted. 3.9 g of the title compound is obtained.

Hydrazine content (colorim.) 0.14% by weight

| Analysis: | C 55.54 | H 7.18 | N 11.64 |
|---|---|---|---|

The gadolinium complex and its salts are obtained as described in example 1j.

| Gadolinium complex | | | |
|---|---|---|---|
| C 45.00 | H 5.46 | N 9.46 | Ge 19.08 |
| | | Sodium salt | |
| C 43.82 | H 5.16 | N 9.20  Na 2.73 | Gd 18.64 |
| | | N-meglumine salt | |
| C 45.17 | H 5.14 | N 9.10 | Gd 15.69 |

EXAMPLE 37

Poly-$N^6$-[10-carboxy-3,6,9-tris-(carboxymethyl)-3,6,9-triazadecanoyl]-poly-L-lysine 632 mg (4.9 mmol of monomer subunits) of polysine is dissolved in 50 ml water with 5 ml of 1 n sodium hydroxide solution and is mixed, with ice cooling by portions, with 2.1 g (5.2 mmol) of $N^3$-(2,6-dioxomorpholinoethyl)-$N^6$-(ethoxycarbonylmethyl)-3,6-diazaoctanedioic acid (example 13a), and the pH is kept above 9 with 1 n sodium hydroxide solution. It is allowed to warm to room temperature with stirring overnight and is dialyzed. After freeze-drying, 2.05 g of small colorless crystalline needles are present.

| Analysis: | C 48.06 | H 6.61 | N 14.21 |
|---|---|---|---|

The gadolinium complex and its salts are obtained as described in example 1j.

| Gadolinium complex | | | |
|---|---|---|---|
| C 36.99 | H 4.66 | N 10.91 | Gd 23.34 |
| | | Sodium salt | |
| C 35.80 | H 4.35 | N 10.63  Na 3.27 | Gd 22.44 |
| | | N-meglumine salt | |
| C 38.78 | H 4.46 | N 10.19 | Gd 18.20 |

EXAMPLE 38

Poly-$N^6$-[10-carboxy-3,6,9-tris-(carboxymethyl)-3,6,9-triazadecanoyl]-poly-L-lysine-poly-[2-(maleimido)-ethylene amide]

Analogously to the formula indicated for example 2, 2.7 g of the complexing agent obtained according to example 37 is reacted. 2.4 g of the title compound is obtained.

Maleimide content (UV) 0.88% by weight

| Analysis: | C 48.10 | H 6.61 | N 14.26 |
|---|---|---|---|

The gadolinium complex and its salts are obtained as described in example 1j.

| Gadolinium complex | | | |
|---|---|---|---|
| C 37.12 | H 4.64 | N 11.02 | Gd 23.14 |
| | | Sodium salt | |
| C 35.87 | H 4.36 | N 10.62  Na 3.29 | Gd 22.99 |
| | | N-meglumine salt | |
| C 38.83 | H 4.49 | N 10.28 | Gd 18.15 |

EXAMPLE 39 a) Poly-$N^6$-[10-carboxy-3,6-bis-(carboxymethyl)-9-ethoxycarbonylmethyl-3,6,9-triazadecanoyl]-poly-L-lysine 0.82 g (5 mmol) of poly-L-lysine hydrochloride is dissolved in 100 ml of water. With a pH of 9.5 being maintained, 6.06 g (15 mmol) of $N^3$-(2,6-dioxomorpholinoethyl)-$N^6$-(ethoxycarbonylmethyl)-3,6-diazoctanedioic acid (example 13a) is added, adjusted to pH 7 with about 11 ml of 1N hydrochloric acid and desalted by an ultrafiltration membrane (Amicon YM2) and then freeze-dried.

Yield: 2.6 g (90% of theory);

Ethoxy determination: 6.85%, which corresponds to an acylation of the polylysine of 88%.

Melting point: 247° C. (decomposition)

1 g of this compound complexed 240 mg of $GD^{3+}$.

b) Poly-$N^6$-[10-carboxy-3,6,9-tris-(carboxymethyl)-3,6,9-triazadecanoyl]-poly-L-lysine-polyhydrazide 2.4 g (4.2 mmol) of the ethyl ester described in example 39a is dissolved in 100 ml of water and after addition of 5 ml (0.5 mmol) of 0.1M hydrazine hydrate solution is stirred 4 hours with reflux and overnight at room temperature. It is ultrafiltered at a pH above 9, the residue solution, after addition of Amberlite IR 120($H^+$) is adjusted to a pH of 4 and freeze-dried.

Yield: 2 g

Hydrazide content: 0.3 mol % c) Gadolinium complex of poly-N⁶-[10-carboxy-3,6,9-tris-(carboxymethyl)-3,6,9-triazadecanoyl]-poly-L-lysine-polyhydrazide 1.9 g of the complexing agent described in example 39b is dissolved in 200 ml of water, mixed with 548 mg of $Gd_2O_3$=475 mg $Gd^{3+}$ and stirred for one hour at 80° C.; the resulting solution is ultrafiltered and then freeze-dried.

Yield: 2.35 g

Gd content: 20% by weight

λ max ($H_2O$)=201 nm (ε=9,000)

The following relaxivities were measured [the measurements of relaxation times T1 and T2 took place in a Minispec p 20 (Bruker) at 0.46 tesla (=20 MHz), 37° C.):

$T_1$ relaxivity: 11.38 (L/mmol sec)

$T_2$ relaxivity: 13.13 (L/mmol sec)

EXAMPLE 40

Poly-N⁶-[10-carboxy-3,6,9-tris-(carboxymethyl)-3,6,9-triazadecanoyl-poly-L-lysine-poly-[10-(hydrazino-carbonyl)-decylamide]

Analogously to the formula indicated for example 4, 2.9 g of the complexing agent produced according to example 37 is reacted. 3.0 g of the title compound is obtained.

Hydrazine content (colorim.) 0.41% by weight

| Analysis: | C 48.3 | H 6.60 | N 14.23 | | |
|---|---|---|---|---|---|
| | | Gadolinium complex | | | |
| | C 37.10 | H 4.68 | N 10.96 | | Gd 23.31 |
| | | Sodium salt | | | |
| | C 35.84 | H 4.39 | N 10.67 | Na 3.28 | Gd 22.49 |
| | | N-meglumine salt | | | |
| | C 38.87 | H 4.48 | N 10.29 | | Gd 18.27 |

EXAMPLE 41 a) 3,6,9-Triaza-3,6,9-tris(tert-butoxycarbonylmethyl)-4-[4-(3-benzyloxycarbonylaminopropoxy)-benzyl]-undecanedioic acid bis-(tert-butyl)diester 4.6 g (5.90 mmol) of the compound of example 1f is combined with 194 mg of NaH (80% in paraffin) (6.48 mmol) in 40 ml of dry tetrahydrofuran and 1.6 g N-(3-bromopropyl)-carbamic acid benzyl ester in 20 ml of tetrahydrofuran is slowly instilled. After stirring overnight, it is concentrated by evaporation and separated from the paraffin oil over a silica gel column. After evaporation of the solvent, 4.2 g of a colorless oil is obtained (yield 74% of theory).

| Analysis | Cld: | C 64.30 | H 8.51 | N 5.76 | O 21.41 |
|---|---|---|---|---|---|
| | Fnd: | C 64.20 | H 8.65 | N 5.82 | | b) 3,6,9-Triaza-3,6,9-tris(tert-butoxycarbonylmethyl)-4-[4-(3-aminopropoxy)-benzyl]-undecanedioic acid bis-(tert-butyl)diester 3.9 g (4.8 mmol) of 3,6,9-triaza-3,6,9-tris(tert butoxycarbonylmethyl)-4-[4-(3-benzyloxycarbonylaminopropoxy)-benzyl]-undecanedioic acid bis-(tert-butyl)diester (example 41a) is dissolved in 100 ml of methanol and hydrogenated with 2.13 g of 10% palladium carbon until no further $H_2$ absorption takes place. Then it is filtered off from the catalyst. The remaining colorless oil weighs 3.17 g (97.3% of theory).

| Analysis | Cld: | C 63.13 | H 9.15 | N 6.69 | O 21.02 |
|---|---|---|---|---|---|
| | Fnd: | C 62.97 | H 9.01 | N 6.62 | | c) Polyacrylpoly-<3-[4-[2,6-di-(bis-(carboxymethyl)-amino)-4-(carboxymethyl)-aza-hexyl]-phenoxy]propyl>-amide A solution of 83.7 g (100 mmol) of the compound produced in the previous reaction step (41b) in 100 ml of toluene instilled in a solution of 10.1 g of polyacrylic acid polyethyl ester in 100 ml of toluene at 60°–80° C. and is kept at this temperature for 20 hours. The solvent is removed and heating takes place for 10 hours with 1 liter of trifluoroacetic acid. After diluting with 10 liters of water, it is dialyzed and freeze-dried by portions. A total of 45.46 g of a colorless fibrous crystalline polymer is obtained.

| Analysis: | C 51.08 | H 6.69 | N 9.45 | | |
|---|---|---|---|---|---|
| | | Gadolinium complex | | | |
| | C 40.69 | H 4.91 | N 7.47 | | Gd 20.96 |
| | | Sodium salt | | | |
| | C 38.17 | H 4.36 | N 7.07 | Na 5.81 | Gd 19.94 |
| | | N-meglumine salt | | | |
| | C 42.13 | H 4.55 | N 7.52 | | Gd 14.05 |

EXAMPLE 42

Polyacrylpoly-<3-[4-[2,6-di-(bis-(carboxymethyl)-amino)-4-(carboxymethyl)-aza-hexyl]-phenoxy]propyl>-amide-poly-]2-(maleimido)-ethylamide]

Analogously to the formula indicated for example 2, 6.2 g of the complexing agent produced according to example 41 is reacted. 6.0 g of the title compound is obtained.

Maleimide content (UV) 0.44% by weight

| Analysis: | C 51.22 | H 6.7 | N 9.45 | | |
|---|---|---|---|---|---|
| | | Gadolinium complex | | | |
| | C 40.61 | H 4.91 | N 7.54 | | Gd 20.99 |
| | | Sodium salt | | | |
| | C 38.36 | H 4.36 | N 7.10 | Na 5.83 | Gd 19.88 |
| | | N-meglumine salt | | | |
| | C 42.35 | H 4.54 | N 7.53 | | Gd 14.04 |

EXAMPLE 43

Polyacrylpoly-<3-{4-[2,6-di-(bis-(carboxymethyl)-amino)-4-(carboxymethyl)-aza-hexyl]-phenoxy}propyl>-amide-poly-[10-(hydrazinocarbonyl)-decylamide]

Analogously to the formula indicated for example 4, 3 g of the complexing agent produced according to example 41 is reacted. 4.4 g of the title compound is obtained.

Hydrazine content (colorim.) 0.56% by weight

| Analysis: | C 51.26 | H 6.73 | N 9.54 | | |
|---|---|---|---|---|---|
| | | Gadolinium complex | | | |
| | C 40.61 | H 4.94 | N 7.58 | | Gd 20.91 |
| | | Sodium salt | | | |
| | C 38.35 | H 4.37 | N 7.15 | Na 5.81 | Gd 19.76 |
| | | N-meglumine salt | | | |
| | C 42.17 | H 4.54 | N 7.57 | | Gd 14.07 |

EXAMPLE 44

Polyacrylpoly-<3-[4-{[2,6-di-(bis-(carboxymethyl)-amino)-4-(carboxymethyl)-aza-hexyl]-phenoxy]propyl>-amide-poly-hydrazide A solution of 3.5 g of polyacrylic acid polyethyl ester in 500 ml of toluene is simultaneously mixed with a solution of 29 g (34 mmol) of the title compound of example 41a and 5 ml of a tetrahydrofuran solution, which contains 150 mg of hydrazine per liter. It is slowly warmed to 80° C. and the procedure as described in example 41c is followed.

Yield: 15.39 g (colorless crystals)

| Analysis: | C 50.90 | H 6.95 | N 9.43 | | |
|---|---|---|---|---|---|
| | | Gadolinium complex | | | |
| | C 40.38 | H 4.88 | N 7.49 | | Gd 21.04 |
| | | Sodium salt | | | |
| | C 38.43 | H 4.37 | N 7.10 | Na 5.81 | Gd 19.87 |
| | | N-meglumine salt | | | |
| | C 41.94 | H 4.53 | N 7.50 | | Gd 14.12 |

EXAMPLE 45 a) 3,6,9-Triaza-3,6,9-tris-(tert-butoxycarbonylmethyl)-4-[3-(benzyloxycarbonyl)-aminopropoxymethyl]-undecanedioic acid bis-(tert-butyl)diester Starting from 3,6,9-triaza-3,6,9-tris-(tert-butoxycarbonylmethyl)-4-hydroxymethyl-undecanedioic acid bis-(tert-butyl)diester (example 25d) the title compound is obtained analogously to the formula for example 41a in 71% yield.

| Analysis | Cld: | C 61.71 | H 8.78 | N 6.26 |
|---|---|---|---|---|
| | Fnd: | C 61.65 | N 8.83 | N 6.35 | b) 3,6,9-Triaza-3,6,9-tris-(tert-butoxycarbonylmethyl)-4-[3-aminopropoxymethyl]-undecanedioic acid bis-(tert-butyl)diester Starting from the benzyloxycarbonyl-protected amino compound obtained in the previous reaction step (example 45a) the title compound is obtained analogously to the formula indicated for example 41b in 93% yield.

| Analysis | Cld: | C 59.97 | H 9.53 | N 7.36 |
|---|---|---|---|---|
| | Fnd: | C 60.11 | N 9.52 | N 7.44 | c) Polyethylenimine polyacetic acid polymethyl ester 8.18 g of polyethylenimine (186.5 mmol of monomer subunits), 20.1 g of triethylamine (200 mmol) and 30 g of bromoacetic acid methyl ester (196 mmol) are mixed with ice cooling in 250 ml of methanol and warmed at room temperature overnight. The solvent is removed and extraction with warm methylene chloride is performed several times. After drying, 19 g of oil remains.

| Analysis: | C 60.03 | H 9.13 | N 14.14 |
|---|---|---|---| d) Polyethylenimine polyacetic acid poly-<3{[2,6-di-(bis-(carboxymethyl)-amino)-4-(carboxymethyl)-aza-hexyl]-methoxy}-propyl>-amide 3.65 g of polyethylenimine polyacetic acid polymethyl ester (example 45c) is dissolved in 50 ml of methanol and mixed with a solution of 31 g (42 mmol) of the title compound of example 45b. It is warmed for 10 hours to 60° C., the solvent is removed and the esters are cleaved with formic acid as described for example 1i. After dialysis and freeze-drying, 15.07 g of the complexing agent is present in the form of fine crystalline needles.

| Analysis: | C 43.24 | H 7.07 | N 13.28 | | |
|---|---|---|---|---|---|
| | | Gadolinium complex | | | |
| | C 33.65 | H 5.04 | N 10.27 | | Gd 27.86 |
| | | Sodium salt | | | |
| | C 31.40 | H 4.44 | N 9.64 | Na 6.29 | Gd 21.59 |
| | | N-meglumine salt | | | |
| | C 37.51 | H 4.61 | N 9.34 | | Gd 14.96 |

EXAMPLE 46

Polyethylenimine polyacetic acid poly-<3{[2,6-di-(bis-(carboxymethyl)-amino)-4-(carboxymethyl)-aza)-hexyl]-oxy}-propyl>-amide-polyhydrazide 3.12 g of polyethylenimine polyacetic acid polymethyl ester (example 45c) is dissolved in 100 ml of methanol and mixed with 1 ml of a solution which contains 50 mg of hydrazine hydrate per 100 ml. It is warmed for 30 minutes to 40° C. and then 26 g (35.2 mmol) of the title compound of example 45b, dissolved in 50 ml of methanol, is added. The further processing takes place as described for example 41c. 12.17 g of fine crystalline substance is obtained.

Hydrazine content: 0.13% by weight

| Analysis: | C 43.35 | H 7.10 | N 13.25 | |
|---|---|---|---|---|
| | | Gadolinium complex | | |
| | C 33.45 | H 5.04 | N 10.31 | Gd 22.97 |

| | Sodium salt | | | | |
|---|---|---|---|---|---|
| C 31.52 | H 4.45 | N 9.68 | | Na 6.28 | Gd 21.61 |
| | N-meglumine salt | | | | |
| C 37.62 | H 4.61 | N 9.30 | | | Gd 14.91 |

EXAMPLE 47

Polyethylenimine polyacetic acid poly-<3-{[2,6-di-(bis-(carboxymethyl)-amino)-4-((carboxymethyl)-aza)-hexyl]-oxy}-propyl>-amide-poly-[2-(maleimido)-ethylamide]

If the hydrazine in example 46 is replaced by an equivalent amount of 2-(maleimido)-ethylamine (which is added in the form of its trifluoroacetate), the corresponding polymer with maleimide functions is obtained.

Maleimide content (UV) 0.38% by weight

| Analysis: | C 43.05 | H 7.10 | N 13.31 | | | Gd 36.46 |
|---|---|---|---|---|---|---|
| | | Gadolinium complex | | | | |
| | C 33.45 | H 5.05 | N 10.28 | | | Gd 22.95 |
| | | Sodium salt | | | | |
| | C 31.52 | H 4.46 | N 9.64 | | Na 6.30 | Gd 21.56 |
| | | N-meglumine salt | | | | |
| | C 37.79 | H 4.61 | N 9.33 | | | Gd 14.90 |

EXAMPLE 48

Polyethylenimine polyacetic acid poly-<3-{[2,6-di-(bis-(carboxymethyl)-amino)-4-((carboxymethyl)-aza)-hexyl]-oxy}-propyl>-amide-poly-[10-(hydrazinocarbonyl)-decylamide]

If the hydrazine in example 46 is replaced by an equivalent amount of 11-amino-undecanoic acid-(2-tert-butoxycarbony)hydrazide, the complex provided with hydrazide as functional group is obtained.

Hydrazide content: 0.77% by weight

| Analysis: | C 43.30 | H 7.09 | N 13.36 | | | |
|---|---|---|---|---|---|---|
| | | Gadolinium complex | | | | |
| | C 33.62 | H 5.07 | N 10.32 | | | Gd 22.92 |
| | | Sodium salt | | | | |
| | C 31.63 | H 4.48 | N 9.74 | | Na 6.30 | Gd 21.50 |
| | | N-meglumine salt | | | | |
| | C 37.68 | H 4.61 | N 9.38 | | | Gd 14.94 |

EXAMPLE 49

Polyethylenimine polyacetic acid poly-<3-[4,5-di-(bis-(carboxymethyl)-amino)-2-hydroxy-cyclohexyl-3-sulfapropyl>-amide 2.15 g (4.9 mmol) of 1,2-bis-[di-(carboxymethyl)-amino]-5-(3-amino-1-thiapropyl)-4-hydroxycyclohexane (European patent application publication No. 0154788) is dissolved with 0.5 g of triethylamine in 50 ml of methanol and combined with a solution of 470 mg (4.75 mmol of monomer subunits) of polyethylenimine polyacetic acid polymethyl ester in 30 ml of methanol. After 18 hours at 60° C., the methanol is evaporated, dissolved in water, dialyzed and the retentate is freeze-dried.

Yield: 2.21 g of white flakes, which sinter above 85° C.

| Analysis: | C 44.25 | H 7.43 | N 12.91 | | S 5.86 | |
|---|---|---|---|---|---|---|
| | | Gadolinium complex | | | | |
| | C 34.47 | H 5.36 | N 10.08 | | S 4.6 | Gd 22.53 |
| | | Sodium salt | | | | |
| | C 33.57 | H 5.05 | N 9.72 | Na 3.18 | S 4.43 | Gd 21.88 |
| | | N-meglumine salt | | | | |
| | C 36.82 | H 5.05 | N 9.55 | | S 3.63 | Gd 17.77 |

EXAMPLE 50

Polyethylenimine polyacetic acid poly-<3-[4,5-di-(bis-(carboxymethyl)-amino)-2-hydroxy-cyclohexyl]-3-sulfapropyl>-amide-poly-[2-(maleimido)-ethylamide]

The production of the title compound takes place analogously to the formula for example 47 by reaction of polyethylenimine polyacetic acid polymethyl ester with 2-(maleimido)-ethylamine and 1,2-(di-[bis-(carboxymethyl)-amino)-5-(3-amino-1-thiapropyl)-4-hydroxycyclohexane.

Maleimide content (UV) 0.51% by weight

| Analysis: | C 44.43 | H 7.39 | N 12.99 | | S 5.84 | |
|---|---|---|---|---|---|---|
| | | Gadolinium complex | | | | |
| | C 34.61 | H 5.33 | N 10.05 | | S 4.58 | Gd 22.38 |
| | | Sodium salt | | | | |
| | C 33.49 | H 5.04 | N 9.79 | Na 3.16 | S 4.44 | Gd 21.86 |
| | | N-meglumine salt | | | | |
| | C 36.96 | H 5.05 | N 9.55 | | S 3.62 | Gd 17.80 |

EXAMPLE 51

Polyethylenimine polyacetic acid poly-<3-[4,5-di-(bis-(carboxymethyl)-amino)-2-hydroxy-cyclohexyl]-3-sulfapropyl>-amide-poly-hydrazide The production of the title compound takes place analogously to the formula for example 46 by reaction of polyethylenimine polyacetic acid polymethyl ester with hydrazine hydrate and 1,2-di-[bis-(carboxymethyl)-amino-5-(3-amino-1-thiapropyl)-4-hydroxycyclohexane.

Hydrazine content (colorim.) 0.17% by weight

| Analysis: | C 44.14 | H 7.44 | N 12.87 | | S 5.88 | |
|---|---|---|---|---|---|---|
| | | Gadolinium complex | | | | |
| | C 34.34 | H 5.36 | N 10.04 | | S 4.6 | Gd 22.55 |
| | | Sodium salt | | | | |
| | C 33.06 | H 5.07 | N 9.80 | Na 3.17 | S 4.45 | Gd 21.89 |
| | | N-meglumine salt | | | | |
| | C 36.73 | H 5.05 | N 9.58 | | S 3.61 | Gd 17.75 |

EXAMPLE 52

Biotinylated gadolinium complex of poly-N-[10-carboxy-3,6,9-tris(carboxymethyl)-3,6,9-triazadecanoyl]-polyethylenimine-polyhydrazide 572 mg (1 mmol) of the gadolinium complex described in example 15 is mixed in 20 ml of water with 220 mg (0.5 mmol) of sulfo-NHS Biotin (Pierce Chemical Company) and is kept at pH 8–9 by addition of NaHCO$_3$. After several hours stirring at room temperature, it is diluted with water and dialyzed until no biotin can any longer be detected in the filtrate. After freeze-drying, 520 mg of colorless substance is obtained. The biotin content is determined colorimetrically (N. M. Green, Methods in Enzymology XVIII, Part A (1970), 418–424): 0.39 mol %.

EXAMPLE 53 a) 3,6-Diaza-3,6-bis-(tert-butoxycarbonylmethyl)-4-(4-benzyloxycarbonylmethoxybenzyl)-suberic acid bis-(tert-butyl)diester 93.06 g of the substance (0.15 mol) obtained according to example 21a is slowly combined with 4.48 g of NaH (80% in paraffin) (0.15 mol) in 600 ml of dry tetrahydrofuran with stirring and then 34.4 g of bromoacetic acid benzyl ester (0.15 mol) in 150 ml of dry tetrahydrofuran is instilled at room temperature. After stirring overnight, it is suctioned off from the precipitated sodium bromide, concentrated by evaporation, taken up in diethyl ether and the remaining inorganic components are removed by washing with water. After drying with MgSO$_4$, it is freed of solvent and purified over a silica gel column. 75.2 g (65% of theory) of a colorless oil is obtained.

| Analysis | Cld: | C 65.43 | H 8.10 | N 3.63 | O 22.82 |
|---|---|---|---|---|---|
|  | Fnd: | C 65.23 | H 8.17 | N 3.58 |  | b) 3,6-Diaza-3,6-bis-(tert-butoxycarbonylmethyl)-4-(4-carboxymethoxybenzyl)-suberic acid bis-(tert-butyl)diester 9.5 g of the compound (0.012 mol) obtained in the previous reaction step is dissolved in 100 ml of dry tetrahydrofuran and hydrogenated in the presence of 2 g of 10 Pd/C until no further hydrogen absorption takes place. After suctioning off, the solvent is removed on a rotation evaporator and the substance is further dried at 0.01 torr. The viscous oil obtained weighs 8.33 g (99% of theory).

| Analysis | Cld: | C 61.74 | H 8.29 | N 4.11 | O 25.64 |
|---|---|---|---|---|---|
|  | Fnd: | C 61.82 | H 8.17 | N 4.12 |  | c) Poly-N$^6$-{4-[2,3-(N,N,N',N'-tetrakis-(tert-butoxycarbonylmethyl)-diamino)-propyl]-phenoxymethylcarbonyl}-poly-L-lysine 9.54 g (14 mmol) of the acid described in example 53b is dissolved in DMF, mixed at −15° C. with 9.7 ml of triethylamine, 1.48 ml (15.4 mmol) chloroformic acid ethyl ester and with a solution of 1.16 g (7 mmol) of poly-L-lysine hydrochloride in water. The resulting suspension is allowed to stir without further cooling, the precipitate is suctioned off, washed with DMF and water and then dried.

Yield: 4 g (72% of theory)

Mp: 212° C. (decomposition)

d) Poly-N$^6$-{4-[2,3-(N,N,N',N'-tetrakis-(carboxymethyl)-diamino)-propyl]-phenoxymethylcarbonyl}-poly-L-lysine, sodium salt 3.5 g of the tetra-tertiary butyl ester described in example 53c is suspended in 80 ml of 24% aqueous hydrobromic acid solution and stirred for 6 days at room temperature. Then the resulting solution is adjusted to pH 7 with sodium hydroxide solution, the residual turbidity is filtered off and the filtrate is ultrafiltered (Amicon Ultrafiltration membrane YM2). After freeze-drying 1.6 g is obtained.

Yield: 74%

Mp: greater than 250° C.

e) Poly-N$^6$-{4-[2,3-(N,N,N',N'-tetrakis-(carboxymethyl)-diamino)-propyl]-phenoxymethylcarbonyl}-poly-L-lysine-polyhydrazide 1.2 g (2 mmol) of the tetraacid sodium salt described in example 53d is dissolved in 60 ml of methanol/water. After addition of 0.026 g (0.2 mmol) of dimethyl sulfate it is stirred for 6 hours at room temperature, then mixed with 5 ml of 80% hydrazine hydrate solution and stirred overnight. Free hydrazine is removed by an ultrafiltration (pH greater than 9) and the resulting residual solution is adjusted to pH about 4 by addition of Amberlite IR (120 H$^+$), filtered from the ion exchanger and freeze-dried.

Yield: 1.0 g

Hydrazide content (colorimetrically) 4.8 mol % f) Gadolinium complex of

Poly-N$^6$-[4-[2,3-(N,N,N',N'-tetrakis-(carboxymethyl)-diamino)-propyl]-phenoxymethylcarbonyl]-poly-L-lysine-polyhydrazide 1.0 g of the complexing agent described in example 53e is mixed in 100 ml of water with 253 mg of Gd$_2$O$_3$ and stirred for one hour at 80° C.; the resulting solution is ultrafiltered and then freeze-dried.

Yield: 1.1 g

Gd content: 18.0% by weight

The following relaxivities were measured (the measurements of relaxation times T1 and T2 took place in a Minispec p 20 (Bruker) at 0.46 tesla (=20 MHz), 37° C.):

T$_1$ relaxivity: 24.08 (L/mmol sec)

T$_2$ relaxivity: 30.24 (L/mmol sec)

EXAMPLE 54

Coupling of the gadolinium complex of poly-N$^6$-{4-[2,3-(N,N,N',N'-tetrakis-(carboxymethyl)-diamino)-propyl]-phenoxymethylcarbonyl}-poly-L-lysine-polyhydrazide on monoclonal antibody 17-1A (MAK) (periodate oxidation method).

The coupling is performed in 0.1 mol/l of sodium acetate buffer of pH 5, which contains 0.1 mol/l of sodium chloride and is named in the following buffer.

10 mg of sodium periodate of oxidized MAK is dissolved in 10 ml of buffer (solution A). 1.6 g of the functionalized polymeric gadolinium complex of example 53g, corresponding to 0.02 mol of hydrazide groups per complexing subunit (665 D), is also dissolved in 10 ml of buffer (solution B).

Solution A is added to solution B with shaking and the batch is incubated over 16 hours at room temperature with light swinging. The MAK concentration in the batch is 0.5 mg/ml and the ratio of hydrazide to aldehyde groups is 100:1. The formed hydrazone is reduced by addition of sodium cyanogen boron hydride (100 mol/mol of MAK). The uncoupled GD complex is separated from the conjugate by means of cation exchanger—chromatography in acetate buffer of pH 4.5.

EXAMPLE 55

Injection solution of a tumor-specific conjugate of monoclonal antibody 17-1A and the gadolinium complex of poly-$N^6$-{4-[2,3-(N,N,N',N'-tetrakis-(carboxymethyl)-diamino)-propyl]-phenoxymethylcarbonyl}-poly-L-lysine-polyhydrazide 200 mg of the conjugate of example 54 is dissolved in 10 ml of sodium bicarbonate buffer (20 nM, 130 nM of NaCl). The solution is sterilized by filtering and freeze-dried in a multivial. The substance is dissolved in 10 ml sterile bidistilled water for intravenous application.

EXAMPLE 56

Gd complex of poly-$N^6$-[10-carboxy-3,6-bis-(carboxymethyl)-9-ethoxycarbonylmethyl-3,6,9-triazadecanoyl]-poly-L-lysine 1.0 g of the complexing agent described in example 39a is dissolved in 100 ml of water and complexed with 277 mg of $Gd_2O_3$=240 mg of $Gd^{3+}$ as described in example 53f.

Yield: 1.2 g

Gd content: 19.3% by weight λ max ($H_2O$)=201 nm (ε=9.000)

The following relaxivities were measured (the measurements of relaxation times T1 and T2 took place in a Minispec p 20 (Bruker) at 0.47 tesla (=20 MHz), 39° C.):

$T_1$ relaxivity: 9.61 (L/mmol sec)

$T_2$ relaxivity: 10.56 (L/mmol sec)

EXAMPLE 57 a) Poly-$N^6$-[10-carboxy-3,6-bis-(carboxymethyl)-9-ethoxycarbonylmethyl-3,6,9-triazadecanoyl]-poly-L-lysine-polyhydrazide 2.4 g (4.2 mmol) of the ethyl ester described in example 39a, analogously to the formula given for example 39b, is partly converted into hydrazide and is worked up at a pH of not greater than 9 as described there.

Yield: 2 g

Hydrazide content: 0.3 mol %, ethoxy determination: 6.3% b) Gd complex of poly-$N^6$-[10-carboxy-3,6-bis-(carboxymethyl)-9-ethoxycarbonylmethyl-3,6,9-triazadecanoyl]-poly-L-lysine-polyhydrazide 1.9 g of the complexing agent described in example a, analogously to example 53f, is complexed with 525 mg of $Gd_2O_3$=455 mg $Gd^{3+}$.

Yield: 2.3 g; Gd content: 17.0% by weight; melting point above 250° C.

EXAMPLE 58 a) Sebacic acid mono-(N'-t-butoxycarbonyl-hydrazide)-monomethyl ester 10.81 g (50 mmol) of sebacic acid monomethyl ester is dissolved in tetrahydrofuran and successively mixed with 8.32 ml (60 mmol) of triethylamine and 5.28 ml (55 mmol) of chloroformic acid ethyl ester [ethyl chloroformate] at –5° C. After 15 minutes 6.61 g (50 mmol) of tert-butylcarbazate in tetrahydrofuran is instilled at this temperature and then stirred at room temperature for 2 hours. The precipitate is suctioned off, the filtrate is concentrated by evaporation and taken up in ethyl acetate. The organic phase is successively washed with $NaHCO_3$ solution, citric acid and water and dried on $Na_2SO_4$. The oil obtained after concentration by evaporation of the ethyl acetate is chromatographed on silica gel in diisopropyl ether.

Yield: 11.2 g (68% of theory)

| Analysis | Cld: | C 58.16 | H 9.15 | N 8.48 |
|---|---|---|---|---|
| | Fnd: | C 58.25 | N 9.13 | N 8.50 | b) Sebacic acid mono-(N'-t-butoxycarbonyl-hydrazide)

9.9 g (30 mmol) of the methyl ester described in example 58a is mixed with 150 ml in NaOH solution and stirred for one hour at room temperature. The clear aqueous solution is washed with ether, acidified with citric acid and the resulting precipitate is taken up in ethyl acetate. After drying on $Na_2SO_4$ and concentration by evaporation of the solvent, an oily residue is obtained.

Yield: 9.3 g (98% of theory)

| Analysis | Cld: | C 56.94 | H 8.92 | N 8.86 |
|---|---|---|---|---|
| | Fnd: | C 56.88 | N 8.98 | N 8.89 | c) Poly-$N^6$-[hydrazinocarbonyl-nonanoyl]-$N^6$-[10-carboxy-3,6-bis(carboxymethyl)-9-ethoxycarbonylmethyl-3,6,9-triazadecanoyl]-poly-lysine 0.48 g (1.5 mmol) of sebacic acid mono(N'-t-butoxycarbonylhydrazide) (example 58b) is dissolved in tetrahydrofuran and successively mixed with 4.16 ml (30 mmol) of triethylamine and 0.15 ml (1.58 mmol) of chloroformic acid ethyl ester at –5° C. After 15 minutes a solution of 2.46 g (15 mmol) of poly-L-lysine hydrochloride in water is added at –20° C. and warmed to room temperature. After 3 hours the tetrahydrofuran is distilled off, diluted with water and mixed by portions at pH=9 with 18.15 g (45 mmol) of $N^3$-(2,6-dioxomorpholinoethyl)-$N^6$-(ethoxycarbonylmethyl)-3,6-diaza-ocatanedioic acid (example 13a) and then adjusted to pH=7 with dilute hydrochloric acid. The solution is filtered, the filtrate is purified by an ultrafiltration membrane (Amicon YM 5) of low-molecular components and then freeze-dried. No impurities can be detected by thin-film chromatography.

Yield: 6.6 g

The resulting polymer Boc-hydrazide is taken up in trifluoroacetic acid without further purification. It is stirred for 1 hour at room temperature and then precipitated with ether, suctioned off and dried. The residue is adjusted in water to pH 7 and freeze-dried.

Yield: 5.5 g

Hydrazide content: 1.5 mol %

1 g of this compound complexes 200 mg of $Gd^{3+}$.

d) Gadolinium complex of poly-$N^6$-[hydrazinocarbonyl-nonanoyl]-$N^6$-10-carboxy-3,6-bis(carboxymethyl)-9-ethoxycarbonylmethyl-3,6,9-triazadecanoyl]-poly-lysine 5 g of the complexing agent described in example 58c is dissolved in 500 ml of water, mixed with 1.13 g of $Gd_2O_3$=

980 mg of Gd$^{3+}$ and stirred for 1 hour at 80° C. The resulting solution is ultrafiltered and then freeze-dried. Yield: 5.6 g; Gd content: 16.1% by weight.

λ max(H$_2$)=200 nm (ε=9,000)

EXAMPLE 59 a) Poly-N$^6$-[hydrazinocarbonyl-nonanoyl]-N$^6$-[10-carboxy-3,6,9-tris(carboxymethyl)-3,6,9-triazadecanoyl]-poly-lysine 5.5 g of the polymeric DTPA ethyl ester described in example 58c is dissolved in as little 2n NaOH solution as possible and after 2 hours at room temperature is neutralized by addition of dilute hydrochloric acid. The clear solution is ultrafiltered (Amicon YM 5) and then freeze-dried.

Yield: 5.1 g

Ethoxy determination: negative 1 g of this compound complexes 200 mg of Gd$^{3+}$.

b) Gadolinium complex of the poly-N$^6$-[hydrazinocarbonyl-nonanoyl]-N$^6$-[10-carboxy-3,6,9-tris(carboxymethyl)-3,6,9-triazadecanoyl]-poly-lysine 5 g of the complexing agent described in example 59a is complexed with Gd$_2$O$_3$ as described in example 58d.

Yield: 5.6 g

Gd content: 16.2% by weight

λ max (H$_2$O)=201 nm (ε=9,000)

EXAMPLE 60 a) Poly-alpha,beta-asparaginic acid-N-[14-carboxy-7,10-bis-(carboxymethyl)-13-ethoxycarbonylmethyl-5-oxo-4,7,10,13-tetraazatetradecyl]-amide 12.1 g (30 mmol) of N$^3$-(2,6-dioxomorpholinoethyl)-N$^6$-(ethoxycarbonylmethyl)-3,6-diaza-octanedioic acid (example 13a) is added by portions to 2.1 g (10 mmol) of alpha,beta-poly-asparaginic acid (N-3-aminopropyl)-amide (H. N. Kovacs et al., J. Med. Chem. 10, 904–908 (1967) in aqueous sodium hydroxide solution (pH 9). The pH of the solution is kept between 9 and 9.5 by simultaneous addition of 1 n NaOH solution. Then it is stirred for 15 minutes more at room temperature and neutralized with dilute hydrochloric acid. The solution is ultrafiltered (Amicon YM 5) and the desalted polymer is freeze-dried.

Yield: 5.5 g (86% of theory)

Ethoxy determination: 6.33% which corresponds to an acylation of the poly-asparaginic amide of 90%

1 g of this compound complexes 258 mg of Gd$^{3+}$.

b) Gadolinium complex of the poly-alpha,beta-asparaginic acid-N-[14-carboxy-7,10-bis-(carboxymethyl)-13-ethoxycarbonylmethyl-5-oxo-4,7,10,13-tetraazatetradecyl]-amide 2.96 (5 mmol) of the complexing agent described in example 60a is mixed with 815 mg of Gd$_2$O$_3$=708 mg of Gd$^{3+}$ at pH 4–5 in water and stirred for 1 hour at 80° C.; the resulting solution is ultrafiltered and then freeze-dried.

Yield: 3.30 g

Gd content: 20.5% by weight

The following relaxivities were measured [the measurements of relaxation times T1 and T2 took place in a Minispet p 20 (Bruker) at 0.46 tesla (=20 MHz), 37° C.]:

T$_1$ relaxivity: 12.4 (L/mmol sec)

T$_2$ relaxivity: 12.5 (L/mmol sec)

EXAMPLE 61 a) Poly-alpha,beta-asparaginic acid-N-[14-carboxy-7,10,13-tris-(carboxymethyl)-5-oxo-4,7,10,13-tetraazatetradecyl]-amide 5.0 g of the polymeric DTPA ethyl ester described in example 60a is dissolved in as little 2n NaOH solution as possible and after 2 hours at room temperature is neutralized by addition of dilute hydrochloric acid. The clear solution is ultrafiltered (Amicon YM 5) and then freeze-dried.

Yield: 4.6 g

Ethoxy determination: negative 1 g of this compound complexes 260 mg of Gd$^{3+}$.

b) Gadolinium complex of the poly-alpha,beta-asparaginic acid-N-[14-carboxy-7,10,13 tris-(carboxymethyl)-5-oxo-4,7,10,13-tetraazatetradecyl]-amide 3.0 g of the complexing agent described in example 61a, analogously to 60b, is complexed with Gd$_2$O$_3$.

Yield: 3.6 g

Gd content: 20.7% by weight

The following relaxivities were measured [the measurements of relaxation times T1 and T2 took place in a Minispec p 20 (Bruker) at 0.46 tesla (=20 MHz), 37° C.]:

T$_1$ relaxivity: 12.9 (L/mmol sec)

T$_2$ relaxivity: 12.7 (L/mmol sec)

EXAMPLE 62 a) 3,6-Bis-(carboxymethyl)-9-(N,N-diethylaminocarbonylmethyl)-3,6,9-triazaundecanedioic acid 20.17 g (50 mmol) of N$^3$-(2,6-dioxomorpholinoethyl)-N$^6$-(ethoxycarbonylmethyl)-3,6-diaza-octanedioic acid (example 13a) is mixed in 250 ml of DMF with 34.7 ml (250 mmol) of triethylamine and 5.22 ml (50 mmol) of diethylamine at 0° C., is stirred overnight at room temperature, concentrated by evaporation in a vacuum, dissolved in 2N NaOH solution and stirred for 2 hours at room temperature. The solution is added over Amberlite IR 120 (H$^+$) and the acidic eluate is freeze-dried.

Yield: 14.1 g (63% of theory)

Melting point: 130° C.

| Analysis | | | | |
|---|---|---|---|---|
| Cld: | C 48.21 | H 7.19 | N 12.49 |
| Fnd: | C 48.01 | N 7.24 | N 12.55 | b) Poly-N$^6$-[10-carboxy-3,6-bis-(carboxymethyl)-9-(N,N-diethylamino-carbonylmethyl)-3,6,9-triazadecanoyl]-poly-L-lysine 8.97 g (20 mmol) of the acid described in example 62a is suspended in 150 ml of acetic anhydride and, after addition of 9.7 ml of pyridine, is stirred overnight at room temperature. The solution is reprecipitated several times from ether and the light yellowish powdery product is added to a solution of 1.6 g (10 mmol) of poly-L-lysine hydrochloride in 200 ml of water, and the pH is kept at 9.5 by addition of dilute sodium hydroxide solution. Then it is stirred for one more hour, neutralized with dilute hydrochloric acid, ultrafiltered (Amicon YM 5) and freeze-dried.

Yield: 4.8 g (88% of theory)
Melting point: above 200° C.
1 g of this compound complexes 236 mg of $Gd^{3+}$ c) Gadolinium complex of the poly-$N^6$-[10-carboxy-3,6-bis-(carboxymethyl)-9-(N,N-diethylamino-carbonylmethyl)-3,6,9-triazadecanoyl]-poly-L-lysine 4.0 g of the complexing agent described in example 62b, analogously to example 60b, is complexed with $Gd_2O_3$.

Yield: 4.8 g
Gd content: 19.1% by weight
$T_1$ relaxivity: 11.75 (L/mmol sec)
$T_2$ relaxivity: 12.93 (L/mmol sec)

EXAMPLE 63 a) 3,6-Bis(carboxymethyl)-9-morpholinocarbonylmethyl-3,6,9-triazaundecanedioic acid 20.17 g (50 mmol) of $N^3$-(2,6-dioxomorpholinomethyl)-$N^6$-(ethoxycarbonylmethyl)-3,6-diaza-octanoic acid (example 13a) is mixed in 250 ml of DMF with 34.7 ml (250 mmol) of triethylamine and 4.8 g (55 mmol) of morpholine in 20 ml of DMF and is worked up as described in example 62a. After freeze-drying of the acid ion exchanger-eluate, 16.2 g (70% of theory) of the title compound is obtained.

| Analysis | Cld: | C 46.75 | H 6.54 | N 12.12 |
|---|---|---|---|---|
|  | Fnd: | C 46.85 | N 6.58 | N 12.07 | b) Poly-$N^6$-10-carboxy-3,6-bis(carboxymethyl)-9-morpholinocarbonylmethyl-3,6,9-triazadecanoyl]-poly-L-lysine 9.25 g (20 mmol) of the acid described in example 63a, analogously to example 62b, is activated with acetic anhydride/pyridine and is reacted with 1.6 g (10 mmol) of poly-L-lysine hydrochloride and worked up as described.

Yield: 4.8 g (85% of theory)
Melting point: above 200° C.
1 g of this compound complexes 230 mg of $Gd^{3+}$ c) Gadolinium complex of poly-$N^6$-10-carboxy-3,6-bis(carboxymethyl)-9-morpholinocarbonylmethyl-3,6,9-triazadecanoyl]-poly-L-lysine 4.0 g of the complexing agent described in example 63b, analogously to example 60b, is complexed with $Gd_2O_3$.

Yield: 4.6 g
Gd content: 18.6% by weight
$T_1$ relaxivity: 12.31 (L/mmol sec)
$T_2$ relaxivity: 13.15 (L/mmol sec)

EXAMPLE 64

Poly-$N^6$-3-{4-[[4-(2,5,8,11-tetrakis-(carboxymethyl)-2,5,8,11-tetraazacyclododecylmethyl]-phenoxy}-2-hydroxypropyl]-poly-L-lysine A solution of 2.5 g of the compound, obtained according to 9e, in 10 ml of tetrahydrofuran is prepared at 0° C. and instilled at 0° C. in a solution of 0.3 g of poly-L-lysine in 15 ml of water. After completion of the addition, it is refluxed for an hour more. After removal of the solvent, it is warmed in 25 ml of warm formic acid and held at 50° C. for two hours. Then, it is poured into 300 ml of water, dialyzed and the retentate is subjected to freeze-drying. 1.1 g of the title compound is obtained as white powder.

| Analysis: | Fnd: | C 51.88 | H 6.35 | N 11.77 |
|---|---|---|---|---|

The gadolinium complex is obtained as described in example 38b.

| Analysis: | Fnd: | C 41.33 | H 4.72 | N 8.92 | Gd 18.88 |
|---|---|---|---|---|---|
|  |  | Sodium salt |  |  |  |
| Analysis: | Fnd: | C 39.75 | H 4.61 | N 8.47 | Gd 17.91 |
|  |  | N-meglumine salt |  |  |  |
| Analysis: | Fnd: | C 42.55 | H 4.52 | N 8.53 | Gd 12.97 |

EXAMPLE 65 a) 2-(4-Benzyloxycarbonylmethoxybenzyl)-1,4,7,10-tetrakis-(tert-butoxy-carbonylmethyl)-1,4,7,10-tetraazacyclododecane 5.0 g of the compound obtained under 9d is slowly mixed with 200 mg of sodium hydride (80% in paraffin) in 35 ml of dry tetrahydrofuran with stirring, then 1.45 g of bromoacetic acid benzyl ester in 50 ml of dry tetrahydrofuran is instilled at room temperature. After stirring overnight, it is suctioned off from the precipitated sodium bromide, concentrated by evaporation, taken up in diethyl ether and the remaining inorganic components are removed by washing with water. After drying on magnesium sulfate, it is purified on a silica gel column. After concentrated by evaporation to dryness, 4.5 g of a colorless oil is obtained.

| Analysis: | Cld: | C 65.60 | H 8.39 | N 7.24 |
|---|---|---|---|---|
|  | Fnd: | C 65.81 | H 8.50 | N 7.11 | b) 2-(4-Carboxymethoxybenzyl)-1,4,7,10-tetrakis-(tert-butoxy-carbonylmethyl)-1,4,7,10-tetraazacyclododecane 3.8 g of the compound obtained according to a) is dissolved in 70 ml of tetrahydrofuran and hydrogenated in the presence of 1.4 g 10% palladium/carbon until no further hydrogen absorption takes place. After filtering, the solvent is evaporated off and the substance is dried at 0.01 torr. 1.7 g of a colorless oil is obtained. (Yield. 51% of theory)

| Analysis: | Cld: | C 62.02 | H 8.48 | N 8.26 |
|---|---|---|---|---|
|  | Fnd: | C 62.18 | H 8.62 | N 8.03 | c) Poly-$N^6$-[4-(2,5,8,11-tetrakis-carboxymethyl-2,5,8,11-tetraazacyclododecylmethyl)-phenoxyacetyl]-poly-L-lysine A solution of 12.8 g of the compound obtained according to b), 2.35 g of chloroformic acid isobutyl ester and 1 g triethylamine in 100 ml of tetrahydrofuran is prepared at 0° C. and this solution is instilled at 0° C. in a solution of 1.6 g of poly-L-lysine and 1.4 g of potassium hydroxide in 80 ml of water. After the addition is completed, it is decanted from the precipitate and treated for two hours at 50° C. with 35 ml of warm formic acid. Then it is poured into water, dialyzed and the retentate is subjected to freeze-drying. 4.1 g of a white powder is obtained.

| Analysis: | Fnd: | C 59.21 | H 3.74 | N 13.82 |
|---|---|---|---|---|

The gadolinium complex is obtained as described in example 38b.

| Analysis: | Fnd: | C 49.76 | H 2.23 | N 11.56 | Gd 21.02 |
|---|---|---|---|---|---|
|  |  | Sodium salt |  |  |  |
| Analysis: | Fnd: | C 47.54 | H 2.11 | N 11.20 | Gd 19.89 |
|  |  | N-meglumine salt |  |  |  |
| Analysis: | Fnd: | C 50.88 | H 2.03 | N 11.47 | Gd 14.32 |

EXAMPLE 65

Example for NMR diagnosis in vivo 0.1 mmol of Gd/kg was applied in the form of the Gd complex of the poly-N-[10-carboxy-3,6,9-tris-(carboxymethyl)-3,6,9-triazadecanoyl]-poly-L-lysine polyhydrazide (example 39c) to a naked mouse (Balb/c nu/nu, female, 25 g) with a subcutaneous HT 29 colon carcinoma i.v.

The substance was dissolved in 300 microliters of 0.9% NaCl. The animal was examined in a nuclear spin tomograph of General Electric Company with a 2-tesla magnet.

Shooting was performed before and after application of the contrast medium with a spin echo sequence ($T_R$=400 msec, $T_E$=30 msec) in the area of the liver and the tumor.

FIG. 1 shows the shot (cross section) in the liver area.

FIG. 2 shows a cross section through the tumor and kidney.

EXAMPLE 66

Coupling of the gadoltnium complex of poly-$N^6$-[hydrazinocarbonyl-nonanoyl]-$N^6$-[10-carboxy-3,6,9-tris-(carboxymethyl)-3,6,9-triazadecanoyl]-polylysine with the monoclonal antibody RA 96 (periodate oxidation method).

The coupling is performed in 0.1M sodium acetate buffer pH 5, which contains 0.1 mol/l of sodium chloride and below is called "buffer." 10 mg of sodium periodate oxidized RA 96 (H. Keltboll, K. Holl, W. Sohmiegel, G. Kloeppel, R. Arndt, S. Matzken, J. Tumor Marker Oncol. 2 (2), 75 (1987) is dissolved in 10 ml of buffer (solution A). 1.6 g of the functionalized polymer Gd complex of example 59 b (about 36 μmol=1.5 mol % of hydrazide groups) is also dissolved in 10 ml of buffer (solution B). Solution A is added to solution B with shaking and the batch is incubated for 16 hours at room temperature with slight rocking movements. The concentration of RA 96 in the batch is 0.5 mg/ml and the ratio of hydrazide to aldehyde groups is greater than 100:1. By addition of sodium cyanoborohydride (100 mol/mol RA 96) the hydrazone formed is reduced (R. F. Borch, M. D. Bernstein, H. D. Dust, J. Amer. Chem. Soc. 93. 2897 (1971). The Gd complex, not coupled, is separated from the conjugate by cation exchange chromatography in acetate buffer pH 4.5.

Example for tumor diagnosis in vivo 3 mg of the conjugate described in example 66 poly-$N^6$-[hydrazinocarbonyl-nonanoyl]-$N^6$-[10-carboxy-3,6,9-tris-(carboxymethyl)-3,6,9-triazadecanoyl]-polylysine with the monoclonal antibody RA 96 (0.05 mmol of Gd/kg) was administered i.v. to a nude mouse (Balb/c nu/nu, female, 18 g) with a subcutaneous WiDr colon carcinoma and a subcutaneous HT 29 colon carcinoma. The substance was dissolved in 300 μl of 0.9% sodium chloride. The animal was examined in a Biospec. 2.35T device of the Bruker company, Karlsruhe. The picture resulted 24 hours p.i. with a spin echo sequence of $T_R$=412 msec and $T_E$=25 msec: the WiDr tumor (right above) is clearly visible by the concentration of the contrast medium.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of NMR imaging comprising administering to a patient an NMR contrast agent, the improvement wherein said agent comprises a pharmaceutically acceptable carrier and a chelate complex of a polymer and at least one paramagnetic ion of an element of atomic numbers 21–29, 42, 44 or 58–70 chelated by said polymer, said polymer containing one or two recurring monomer units wherein at least one of said recurring units exhibits a pendant ligand group containing carboxylic acid groups suitable for chelating and said complex optionally further contains one or more cations of inorganic and/or organic bases, amino acids or amino acid amides bonded to said carboxy groups, wherein the monomer units of said polymer are

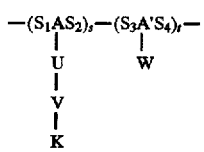

in which

A and A' each independently is

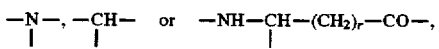

r is 0 or 1, s is a whole number from 7 to 20,000, t is 0–20,000,

U is a direct bond,

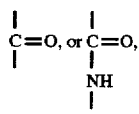

V is a $C_0$–$C_{20}$ hydrocarbylene group optionally containing one or more imino, phenylene, phenyleneoxy, phenylene-imino, amide, hydrazide, or ester group(s), or oxygen, sulfur and/or nitrogen atom(s) and optionally substituted by hydroxy, mercapto, imino, epoxy, oxo, thioxo and/or amino group(s), $S_1$ is a direct bond, —CH$_2$— or —CH$_2$CH$_2$—;

$S_2$ is a direct bond;

$S_3$ is the same as $S_1$;

$S_4$ is the same as $S_2$;

K is a complexing agent of general formula IA, IB, IC or ID

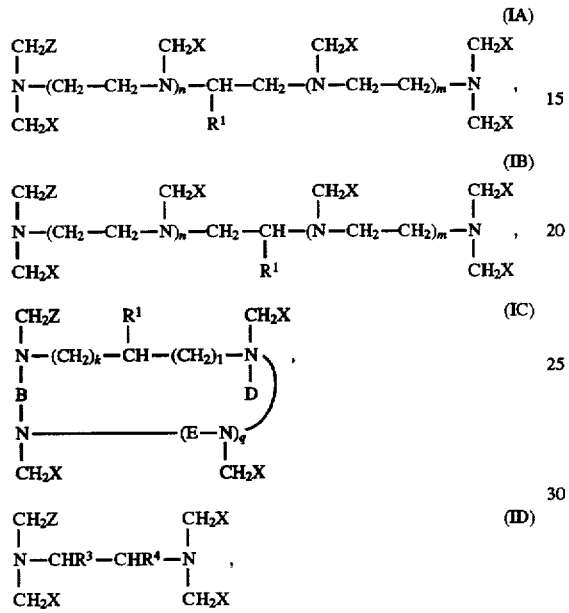

in which n and m each is independently 0, 1, 2, 3 or 4, and n and m together add to no more than 4, k is 1, 2, 3, 4 or 5, l is 0, 1, 2, 3, 4 or 5, q is 0, 1 or 2, each X independently is —COOH, B, D and E, can be the same or different and each independently is

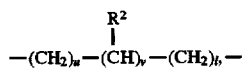

wherein $R^2$ is hydrogen or a $C_1$-$C_{20}$ hydrocarbyl group, optionally containing oxygen and/or nitrogen atom(s), and optionally substituted by hydroxy and/or amino group(s), u is 0, 1, 2, 3, 4 or 5, v is 0 or 1, l' is 0, 1, 2, 3, 4 or 5, and B, D and E each contain at least 2 and at most 5 carbon atoms in their chain, Z is

or an X group, $R^1$ is a direct bond or hydrogen, provided that Z is

only if $R^1$ at the same time is hydrogen, and that Z is X, only if $R^1$ at the same time is a direct bond, $R^3$ and $R^4$ together are dimethylenemethine or trimethylenemethine, each optionally substituted by 1-2 hydroxy or 1-3 $C_1$-$C_4$ alkyl groups, W is hydrogen or $U_w$—$V_w$—$K_w$, and $U_w$, $V_w$ and $K_w$ each have one of the meanings given for U, V and K, wherein, optionally, a part of the COOH groups is esterified or amidated, wherein, in the polymer backbone, at most two consecutive N atoms are bonded together, wherein

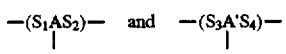

of said monomer units form a polyethyleneimine, polylysine, polyasparaginic acid, polyethyleneiminopolyacetic acid ester, or polyacryl ester backbone, and at least 67% of said monomer units exhibit a pendant ligand group containing carboxylic acid groups suitable for chelating.

2. A method according to claim 1, wherein said monomer units of said polymer are

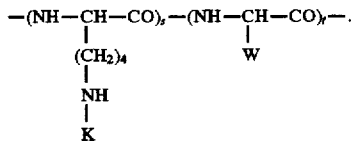

3. A method according to claim 1, wherein said functional group at the end of V' is

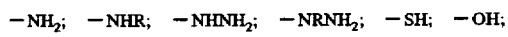

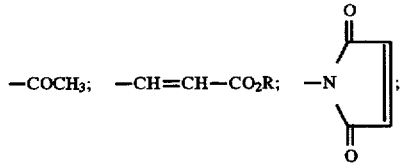

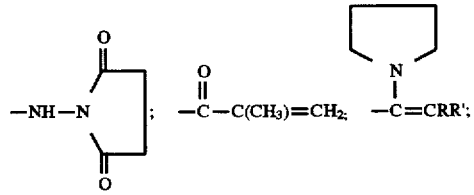

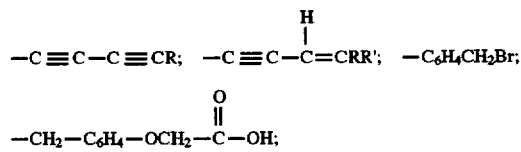

-continued

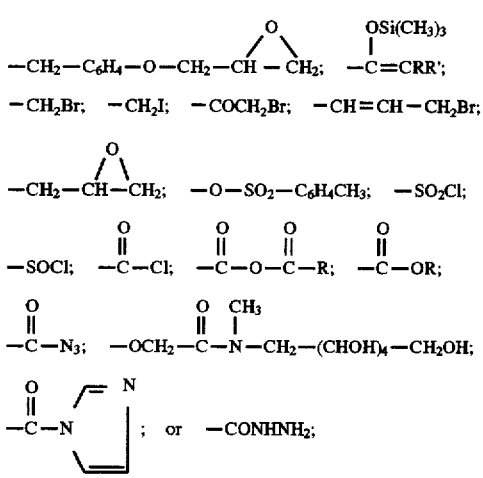

wherein R and R' are the same or different and each is hydrogen, phenyl or $C_{1-20}$-alkyl, $C_{2-20}$-alkylene or $C_{2-20}$-alkynylene, each optionally substituted by phenyl.

4. A method according to claim 1 wherein V is:

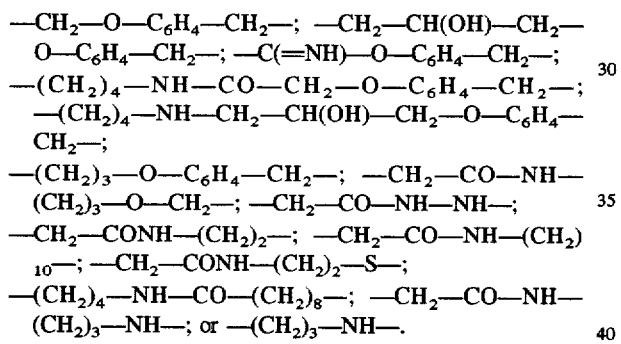

5. A method according to claim 1, wherein said agent further comprises physiologically compatible buffers, electrolytes, and/or antioxidants.

6. A method according to claim 1, wherein said agent contains 1 micromole-1 mole of said metal ion in the form of its polymer complex per liter.

7. A method according to claim 1, wherein said complexed polymer is administered at a dose of 0.001–5 mmole of said metal ion per kg of body weight.

8. A method according to claim 1, wherein said complexed polymer is administered enterally or parenterally.

9. A method of enhancing NMR imageability of a patient comprises administering to the patient an agent comprising a pharmaceutically acceptable carrier and an amount, selective to enhance NMR image contrast, of a physiologically compatible chelate complex of at least one paramagnetic metal ion of an element of atomic numbers 21–29, 42, 44 or 58–70 and a polymer, said polymer containing one or two recurring monomer units wherein at least one of said recurring units exhibits a pendant ligand group containing carboxylic acid groups suitable for chelation, and optionally further containing one or more cations of inorganic and/or organic bases, amino acids or amino acid amides bonded to said carboxy groups, wherein the monomer units of said polymer are

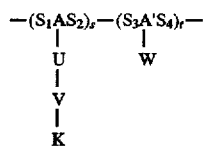

in which

A and A' each independently is

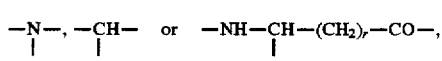

r is 0 or 1,
s is a whole number from 7 to 20,000,
t is 0–20,000,
U is a direct bond,

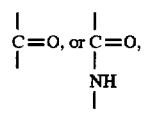

V is a $C_0$–$C_{20}$ hydrocarbylene group optionally containing one or more imino, phenylene, phenyleneoxy, phenyleneimino, amide, hydrazide, or ester group(s), or oxygen, sulfur and/or nitrogen atom(s) and optionally substituted by hydroxy, mercapto, imino, epoxy, oxo, thioxo and/or amino group(s), $S_1$ is a direct bond, —$CH_2$— or —$CH_2CH_2$—;
$S_2$ is a direct bond;
$S_3$ is the same as $S_1$;
$S_4$ is the same as $S_2$;
K is a complexing agent of general formula IA, IB, IC or ID

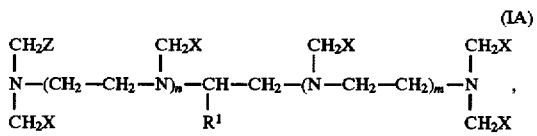

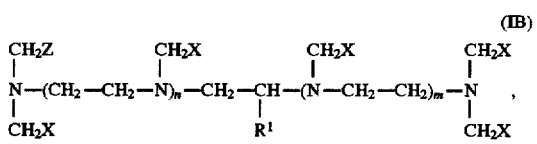

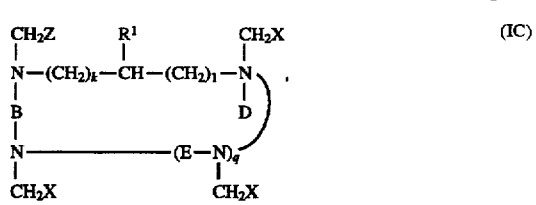

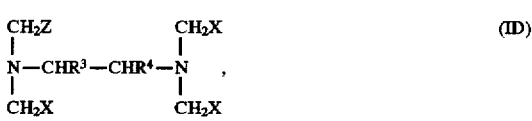

in which
n and m each is independently 0, 1, 2, 3 or 4, and n and m together add to no more than 4, k is 1, 2, 3, 4 or 5,
l is 0, 1, 2, 3, 4 or 5,
q is 0, 1 or 2,
each X independently is —COOH
B, D and E, can be the same or different and each independently is

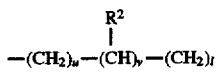

wherein
R$^2$ is hydrogen or a C$_1$-C$_{20}$ hydrocarbyl group, optionally containing oxygen and/or nitrogen atom(s), and optionally substituted by hydroxy and/or amino group(s),
u is 0, 1, 2, 3, 4 or 5,
v is 0 or 1,
l' is 0, 1, 2, 3, 4 or 5,
and B, D and E each contain at least 2 and at most 5 carbon atoms in their chain,
Z is

or an X group,
R$^1$ is a direct bond or hydrogen, provided that Z is

only if R$^1$ at the same time is hydrogen, and that Z is X, only if R$^1$ at the same time is a direct bond,
R$^3$ and R$^4$ together are dimethylenemethine or trimethylenemethine, each optionally substituted by 1-2 hydroxy or 1-3 C$_1$-C$_4$ alkyl groups,
W is hydrogen or U$_w$—V$_w$—K$_w$,
and
U$_w$, V$_w$ and K$_w$ each have one of the meanings given for U, V and K,
wherein, optionally, a part of the COOH groups is esterified or amidated,
wherein, in the polymer backbone, at most two consecutive N atoms are bonded together,
wherein

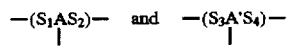

of said monomer units form a polyethyleneimine, polylysine, polyasparaginic acid, polyethyleneiminopolyacetic acid ester, or polyacryl ester backbone, and
at least 67% of said monomer units exhibit a pendant ligand group containing carboxylic acid groups suitable for chelating.

10. A method according to claim 1, wherein the backbone of said polymer is polyethyleneimine.

11. A method according to claim 1, wherein the backbone of said polymer is polylysine.

12. A method according to claim 1, wherein the backbone of said polymer is polyasparaginic acid.

13. A method according to claim 1, wherein the backbone of said polymer is polyethyleneiminopolyacetic acid ester.

14. A method according to claim 1, wherein the backbone of said polymer is polyacryl ester.

15. A method according to claim 1, wherein K is a radical of ethylenediaminetetraacetic acid, diethylenetriaminepentaacetic acid, trans-1,2-cyclohexanediaminotetraacetic acid, 1,4,7,10-tetraazacyclododecanetetraacetic acid, 1,4,7-triazacyclononanetriacetic acid, 1,4,8,11-tetraazatetradecanetetraacetic acid or 1,5,9-triazacyclododecanetriacetic acid.

16. A method according to claim 10, wherein W is H, 2-(maleimido)-ethyleneamide, a hydrazide, or 10-(hydrazinocarbonyl)-decylamide.

17. A method according to claim 10, wherein U is a single bond and V is a single bond, 4-phenoxyacetal, 3-(4-phenoxy)-2-hydroxypropyl, a phenyliminocarbonate or —CH$_2$—O—CH$_2$—CHOH—CH$_2$—.

18. A method of conducting NMR imaging, comprising NMR imaging a patient to whom there has been administered an agent comprising a pharmaceutically acceptable carrier and an amount effective to enhance NMR image contrast of a physiologically compatible chelate complex of a paramagnetic metal ion of an element of atomic numbers 21–29, 42, 44 or 58–70 and a polymer, said polymer containing one or two recurring monomer units wherein at least one of said recurring units exhibits a pendant ligand group containing carboxylic acid groups suitable for chelation, and optionally further containing one or more cations of inorganic and/or organic bases, amino acids or amino acid amides bonded to said carboxy groups, whereby an NMR image of enhanced contrast is obtained, and wherein the monomer units of said polymer are

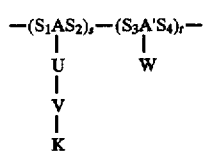

in which
A and A' each independently is

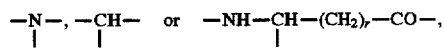

r is 0 or 1,
s is a whole number from 7 to 20,000,
t is 0–20,000,
U is a direct bond,

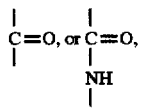

V is a C$_0$-C$_{20}$ hydrocarbylene group optionally containing one or more imino, phenylene, phenyleneoxy, phenyleneimino, amide, hydrazide, or ester group(s), or oxygen, sulfur and/or nitrogen atom(s) and optionally substituted by hydroxy, mercapto, imino, epoxy, oxo, thioxo and/or amino group(s), S$_1$ is a direct bond, —CH$_2$— or —CH$_2$CH$_2$—;
S$_2$ is a direct bond;
S$_3$ is the same as S$_1$;
S$_4$ is the same as S$_2$;

K is a complexing agent of general formula IA, IB, IC or ID

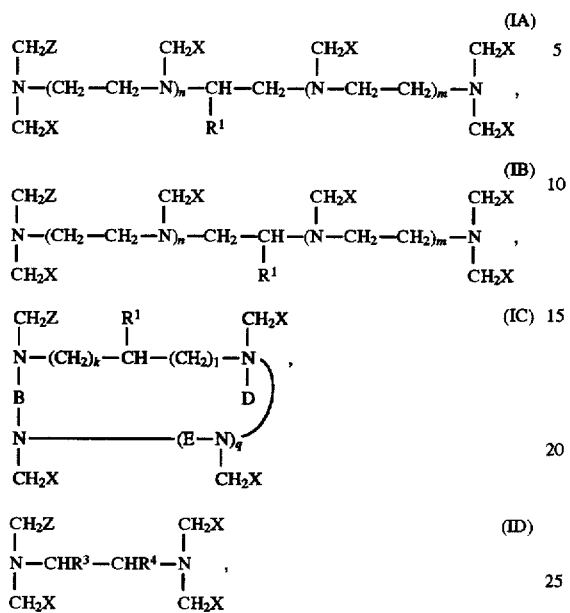

in which
n and m each is independently 0, 1, 2, 3 or 4, and n and m together add to no more than 4,
k is 1, 2, 3, 4 or 5,
l is 0, 1, 2, 3, 4 or 5,
q is 0, 1 or 2,
each X independently is —COOH
B, D and E, can be the same or different and each independently is

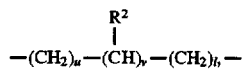

wherein
$R^2$ is hydrogen or a $C_1$–$C_{20}$ hydrocarbyl group, optionally containing oxygen and/or nitrogen atom(s), and optionally substituted by hydroxy and/or amino group(s),
u is 0, 1, 2, 3, 4 or 5,
v is 0 or 1,
l' is 0, 1, 2, 3, 4 or 5,
and B, D and E each contain at least 2 and at most 5 carbon atoms in their chain,
Z is

or an X group,
$R^1$ is a direct bond or hydrogen, provided that Z is

only if $R^1$ at the same time is hydrogen, and that Z is x, only if $R^1$ at the same time is a direct bond,
$R^3$ and $R^4$ together are dimethylenemethine or trimethylenemethine, each optionally substituted by 1–2 hydroxy or 1–3 $C_1$–$C_4$ alkyl groups,
W is hydrogen $U_w$—$V_w$—$K_w$.

and $U_w$, $V_w$ and $K_w$ each have one of the meanings given for U, V and K,
wherein, optionally, a part of the COOH groups is esterified or amidated,
wherein, in the polymer backbone, at most two consecutive N atoms are bonded together,
wherein

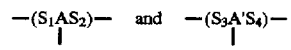

of said monomer units form a polyethyleneimine, polylysine, polyasparaginic acid, polyethyleneiminopolyacetic acid ester, or polyacryl ester backbone, and
at least 67% of said monomer units exhibit a pendant ligand group containing carboxylic acid groups suitable for chelating.

* * * * *